US009504745B2

(12) United States Patent
Harrison, Jr. et al.

(10) Patent No.: US 9,504,745 B2
(45) Date of Patent: *Nov. 29, 2016

(54) COMPOSITIONS AND METHODS FOR CANCER TREATMENT USING TARGETED CARBON NANOTUBES

(71) Applicant: The Board of Regents of the University of Oklahoma, Norman, OK (US)

(72) Inventors: Roger G. Harrison, Jr., Norman, OK (US); Daniel E. Resasco, Norman, OK (US); Luis Filipe Ferreira Neves, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 133 days.

This patent is subject to a terminal disclaimer.

(21) Appl. No.: 14/100,892

(22) Filed: Dec. 9, 2013

(65) Prior Publication Data

US 2014/0155333 A1  Jun. 5, 2014

Related U.S. Application Data

(63) Continuation-in-part of application No. 13/800,218, filed on Mar. 13, 2013, now abandoned, which is a continuation-in-part of application No. 12/618,553, filed on Nov. 13, 2009, now Pat. No. 8,518,870, which is a continuation-in-part of application No. 12/130,841, filed on May 30, 2008, now abandoned, which is a continuation-in-part of application No. 12/033,857, filed on Feb. 19, 2008, now abandoned.

(60) Provisional application No. 61/734,802, filed on Dec. 7, 2012, provisional application No. 60/901,894, filed on Feb. 19, 2007, provisional application No. 61/114,714, filed on Nov. 14, 2008.

(51) Int. Cl.
| A61K 41/00 | (2006.01) |
| A61N 1/40 | (2006.01) |
| A61K 38/17 | (2006.01) |
| A61K 45/06 | (2006.01) |
| A61K 47/48 | (2006.01) |
| B82Y 5/00 | (2011.01) |
| A61N 2/02 | (2006.01) |
| A61N 5/06 | (2006.01) |

(52) U.S. Cl.
CPC ....... *A61K 41/0052* (2013.01); *A61K 38/1709* (2013.01); *A61K 45/06* (2013.01); *A61K 47/48215* (2013.01); *A61K 47/48246* (2013.01); *A61K 47/48869* (2013.01); *A61K 47/48884* (2013.01); *A61N 1/406* (2013.01); *A61N 2/02* (2013.01); *B82Y 5/00* (2013.01); *A61N 5/062* (2013.01); *A61N 2005/0659* (2013.01)

(58) Field of Classification Search
None
See application file for complete search history.

(56) References Cited

U.S. PATENT DOCUMENTS

| 6,890,654 | B2 | 5/2005 | Stupp et al. |
| 7,125,541 | B2 | 10/2006 | Thorpe et al. |
| 7,422,738 | B2 | 9/2008 | Thorpe et al. |
| 7,500,953 | B2 | 3/2009 | Oraevsky et al. |
| 7,510,555 | B2 | 3/2009 | Kanzius |
| 8,518,870 | B2 * | 8/2013 | Harrison, Jr. .... A61K 47/48884 514/1.1 |
| 2003/0113714 | A1 | 6/2003 | Belcher et al. |
| 2004/0180094 | A1 | 9/2004 | Joyce |
| 2004/0208868 | A1 | 10/2004 | Thorpe et al. |
| 2005/0251233 | A1 | 11/2005 | Kanzius |
| 2005/0251234 | A1 | 11/2005 | Kanzius |
| 2005/0273143 | A1 | 12/2005 | Kanzius |
| 2006/0083745 | A1 | 4/2006 | Thorpe et al. |
| 2006/0199770 | A1 * | 9/2006 | Bianco ............. A61K 47/48238 424/486 |
| 2006/0275371 | A1 | 12/2006 | Dai et al. |
| 2007/0250139 | A1 | 10/2007 | Kanzius |

FOREIGN PATENT DOCUMENTS

WO   WO 2004/068405    12/2004
WO   PCT/US2008/02214   7/2008

OTHER PUBLICATIONS

Minami, 2006, Applied Physics Letters, 88, 093123.*
Cabral et al., "Covalent and Coordination Immobilization of Proteins" in "Protein Immobilization Fundamentals and Applications", ed. R.F. Taylor, (1991), pp. 73-138, Marcel Dekker, Inc.
Gannon et al., "Carbon Nanotube-enhanced Thermal Destruction of Cancer Cells in a Noninvasive Radiofrequency Field" Cancer, vol. 110, No. 12 (Dec. 15, 2007), pp. 2654-2665.
Gerke et al., "Annexins: From Structure to Function" Physiol. Rev., vol. 82, pp. 331-371, Apr. 2002.
Hahn et al., "Thermochemotherapy: Synergism Between Hyperthermia (42-43) and Adriamycin (or Bleomycin) in Mammalian Cell Inactivation" proc. Nat. Acad. Sci., vol. 72, No. 3, pp. 937-940, Mar. 1975.
Kam et al. "Carbon nanotubes as multifunctional biological transporters and near-infrared agents for selective cancer cell destruction" PNAS, vol. 102, No. 33, pp. 11600-11605, Aug. 16, 2005.
Lolli et al., "Tailoring (n, m) Structure of Single-Walled Carbon Nanotubes by Modifying Reaction Conditins and the Nature ofhte Support of CoMo Catalysts" J. Phys. Chem. B, vol. 110, pp. 2108-2115, 2006.
Palwai et al., "Retention of biological activity and near-infrared absorbance upon adsorption of horseradish peroxidase on single-walled carbon nanotubes" Nanotechnology, vol. 18, 235601 (5 pp), 2007.

(Continued)

Primary Examiner — Satyanarayana R Gudibande
(74) Attorney, Agent, or Firm — Dunlap Codding, P.C.

(57) ABSTRACT

Compositions for detecting and/or destroying cancer tumors and/or cancer cells via photodynamic therapy are disclosed, as well as methods of use thereof. The compositions comprise a linking protein or peptide attached to or otherwise physically associated with a carbon nanotube to form a targeted protein-carbon nanotube complex.

25 Claims, 13 Drawing Sheets

(56) References Cited

OTHER PUBLICATIONS

Ran et al., "Increased Exposure of Anionic Phospholipids on the Surface of Tumor Blood Vessels" Cancer Research, vol. 62, pp. 6132-6140, Nov. 1, 2002.

Shao et al., "Integrated molecular targeting of IGF1R and HER2 surface receptors and destruction of breast cancer cells using single wall carbon nanotubes" Nanotechnology, vol. 18, 315101 (9 pp), 2007.

Sibata et al., "Photodynamic therapy in oncology" Expert Opin. Pharmacother, vol. 2, No. 6, pp. 917-927, 2001.

Van der Zee, "Heating the patient: a promising approach?" Annals of Oncology, vol. 13, pp. 1173-1184, 2002).

Minami et al., "Cellulose derivatives as excellent dispersants for single-wall carbon nanotubes as demonstrated by absorption and photoluminescence spectroscopy," Applied Physics Letters 88 093123 (2006).

Liu et al., "Nanotechnology tackles tumours," News & Views, Nature vol. 2:20-21 (2007).

A Thesis Submitted to The Undergraduate Faculty of the University of Oklahoma by Luis Filipe Ferreira Neves—2007.

Yang et al., "In Vivo and In Vitro Measurement of Apoptosis in Breast Cancer Cells Using $^{99m}$Tc-EC-Annexin V," Cancer Biotherapy & Radiopharmaceuticals vol. 16:173-85 (2001).

Mochizuki et al., "Detection of Apoptotic Tumor Response In Vivo After a Single Dose of Chemotherapy with $^{99m}$Tc-Annexin V," Journal of Nuclear Medicine vol. 44 No. 1:92-97 (2003).

Pantarotto et al., "Immunization with Peptide-Functionalized Carbon Nanotubes Enhances Virus-Specific Neutralizing Antibody Responses," Chemistry & Biology, vol. 10, 961-966 (2003).

Handbook of Pharmaceutical Excipients, American Pharmaceutical Association & The Pharmaceutical Society of Great Britain, "Carboxymethylcellulose Sodium," pp. 45-48 (1988).

U.S. Appl. No. 12/033,857 Office Action dated Feb. 19, 2008.

U.S. Appl. No. 12/033,857 Notice of Abandonment mailed Apr. 26, 2011.

U.S. Appl. No. 12/130,841 Office Action dated Jul. 13, 2010.

U.S. Appl. No. 12/130,841 Notice of Abandonment mailed Feb. 16, 2011.

U.S. Appl. No. 12/618,553 Office Action dated Apr. 11, 2012.

U.S. Appl. No. 12/618,553 Amendment & Response to Office Action dated Apr. 11, 2012.

U.S. Appl. No. 12/618,553 Office Action dated Aug. 2, 2012.

U.S. Appl. No. 12/618,553 Amendment & Response to Office Action dated Aug. 2, 2012.

U.S. Appl. No. 12/618,553 Final Office Action dated Mar. 14, 2013.

U.S. Appl. No. 12/618,553 Amendment & Response to Final Office Action dated Mar. 14, 2013.

U.S. Appl. No. 12/618,553 Notice of Allowance & Fees Due dated Jun. 20, 2013.

U.S. Appl. No. 12/618,553 Issue Fee & Publication Fee Paid dated Jul. 16, 2013, Patent Issue dated Aug. 27, 2013—U.S. Pat. No. 8,518,870.

U.S. Appl. No. 13/800,218 Express Abandonment filed Dec. 10, 2013.

* cited by examiner (a) (b)

(c) (d)

(e) (f)

COMPOSITIONS AND METHODS FOR CANCER TREATMENT USING TARGETED CARBON NANOTUBES

CROSS-REFERENCE TO RELATED APPLICATIONS/INCORPORATION BY REFERENCE STATEMENT

The present application claims the benefit under 35 U.S.C. 119(e) of U.S. Provisional Application Ser. No. 61/734,802, filed Dec. 7, 2012. The present application is also a continuation-in-part of U.S. Ser. No. 13/800,218, filed Mar. 13, 2013, now abandoned; which is a continuation-in-part of U.S. Ser. No. 12/618,553, filed Nov. 13, 2009, now U.S. Pat. No. 8,518,870, issued Aug. 27, 2013; which is a continuation-in-part of U.S. Ser. No. 12/130,841, filed May 30, 2008, now abandoned; which is a continuation-in-part of U.S. Ser. No. 12/033,857, filed Feb. 19, 2008, now abandoned; which claims the benefit under 35 U.S.C. 119(e) of U.S. Provisional Application Ser. No. 60/901,894, filed Feb. 19, 2007. The '553 application also claims the benefit under 35 U.S.C. 119(e) of U.S. Provisional Application Ser. No. 61/114,714, filed Nov. 14, 2008. The entire contents of each of the above-referenced patents and patent applications are hereby expressly incorporated herein by reference.

STATEMENT REGARDING FEDERALLY SPONSORED RESEARCH OR DEVELOPMENT

This invention was made with government support under Grant No. DE-FG02-06ER64239 awarded by the Department of Energy and Grant No. W81XWH-07-1-0563 awarded by the Department of Defense. The Government has certain rights in the invention.

BACKGROUND

Photodynamic therapy (PDT) shows promise as a treatment of cancer. PDT, first used in 1975, is based on the concept that light irradiation can change an inert substance into an active one. In PDT, a specific light-sensitive agent, the so-called photosensitizer, is administered systemically to a cancer patient. Light of a specific wavelength is delivered to the tumor and activates the photosensitizer. The activated molecule transfers an electron to an adjacent oxygen molecule and generates oxygen radicals, or the energy is transferred from the activated photosensitive molecule to an oxygen molecule, generating an excited singlet oxygen molecule. These reactive oxygen species have very short lifetimes, but are extremely reactive and usually induce a cytotoxic reaction or cell destruction, respectively.

There have been several studies published describing the use of PDT to treat cancer in both animals and humans, including the treatment of lung and brain cancers. However, one main limitation of the photosensitizers used is that they absorb light at a relatively short wavelength (typically 600-700 nm), meaning that light cannot penetrate deep into the tissue (generally up to 1 cm). A commonly used clinical photosensitizer is Photofrin porfimer sodium, which has the side effect of causing prolonged skin photosensitivity that results in patients having to be protected from sunlight for several weeks. Despite these limitations, PDT has now achieved the status of a standard treatment modality for centrally located early-stage lung cancer.

A less invasive type of PDT is performed with a bronchoscope for the treatment of bronchopulmonary malignant neoplasia. In this therapy, the endobronchial tumor is pre-sensitized by administration of the sensitizing photochemical. After a time interval, bronchoscopic illumination (exposure to laser light) is performed to achieve cancer necrosis. PDT is now indicated in both early and advanced stage cancers of this type.

Another application of PDT is done in combination with surgery. For example, in a phase II trial with 22 patients with non-small-cell lung cancer (NSCLC) with pleural spread, the patients received the photosensitizer porfirmer sodium 24 hours before surgery, at which time all the gross tumor was resected and followed by illumination of the hemithorax with 603 nm light. The median survival was 21 months, which was viewed as encouraging and warranting further evaluation of this therapy.

The availability of alternative methods of using photodynamic therapy to treat cancers is desirable.

DETAILED DESCRIPTION

Figure 1:
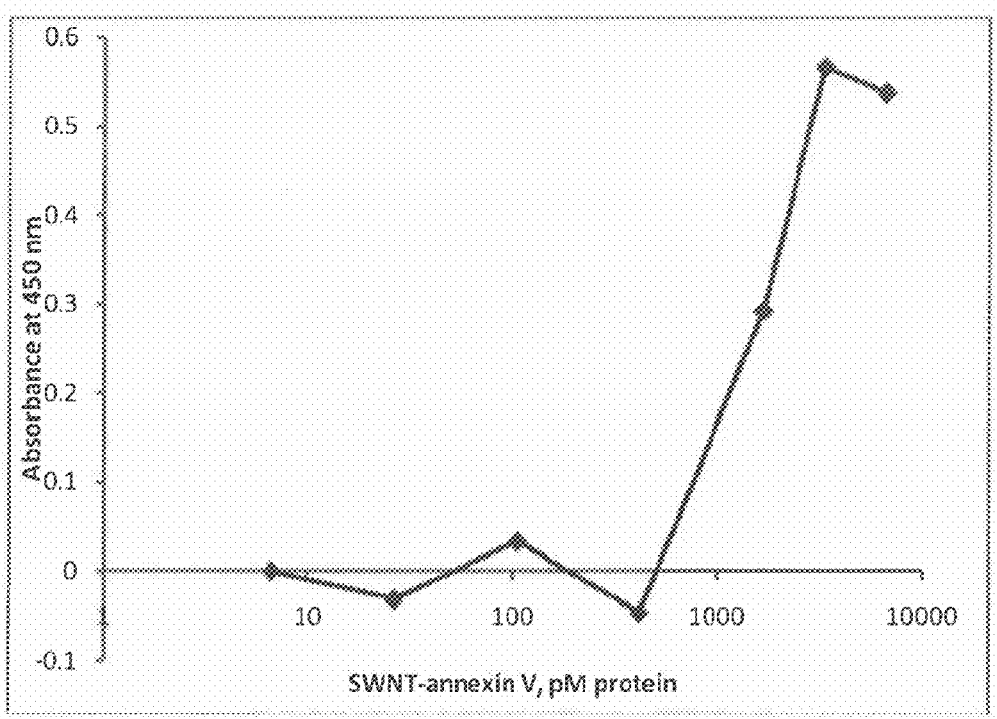
FIG. 1 is a graph showing binding of SWNT-annexin V (biotinylated) to human endothelial cells with surface exposure of phospatidylserine induced by the addition of $H_2O_2$ (1 mM).

Before explaining at least one embodiment of the presently disclosed and claimed inventive concept(s) in more detail by way of exemplary description, examples, and results, it is to be understood that the presently disclosed and claimed inventive concept(s) is not limited in its application to the details of methods and compositions as set forth in the following description. The presently disclosed and claimed inventive concept(s) is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the presently disclosed and claimed inventive concept(s) may be practiced without these specific details. In other instances features which are well known to persons of ordinary skill in the art have not been described in detail to avoid unnecessary complication of the description.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed.), Cold Spring Harbor Laboratory Press, Cold Spring Harbor, N.Y. (1989) and Ausubel et al. Current Protocols in Molecular Biology (Wiley Interscience (1988)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of animals.

All patents, published patent applications, and non-patent publications mentioned in the specification are indicative of the level of skill of those skilled in the art to which the presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and methods of production and application thereof disclosed herein can be made and executed without undue experimentation in light of the present disclosure. While the compositions and methods of the presently disclosed and claimed inventive concept(s) have been described in terms of certain embodiments, it will be apparent to those of skill in the art that variations may be applied to the compositions and/or methods and in the steps or in the sequence of steps of the methods described herein without departing from the concept, spirit and scope of the presently disclosed and claimed inventive concept(s). All such similar substitutes and modifications apparent to those skilled in the art are deemed to be within the spirit, scope and concept of the presently disclosed and claimed inventive concept(s).

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." Throughout this application, the term "about" is used to indicate that a value includes the inherent variation of error for the composition, the method used to administer the composition, or the variation that exists among the study subjects. The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

Throughout the specification and claims, unless the context requires otherwise, the terms "substantially" and "about" will be understood to not be limited to the specific terms qualified by these adjectives/adverbs, but will be understood to indicate a value includes the inherent variation of error for the device, method or composition used, the method being employed to determine the value and/or the variation that exists among study subjects. Thus, said terms allow for minor variations and/or deviations that do not result in a significant impact thereto. For example, in certain instances the term "about" is used to indicate that a value includes the inherent variation of error for the device, method or composition used, the method being employed to determine the value and/or the variation that exists among study subjects. Similarly, the term "substantially" may also refer to at least 75%, at least 80%, at least 85%, at least 90%, at least 91%, at least 92%, at least 93%, at least 94%, at least 95%, at least 96%, at least 97%, at least 98%, or at least 99% or higher, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

The term "protein product" as used herein includes natural, recombinant or synthetic proteins, biologically active protein variants (including insertion, substitution and deletion variants), and chemically modified derivatives thereof. Included are protein products that are substantially homologous to the human protein products. The term "biologically active" as used herein means that the protein product demonstrates similar properties, but not necessarily all of the same properties, and not necessarily to the same degree, as the natural human protein products. Further, by "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other component in the composition thereof). For example, a substantially purified fraction is a composition wherein the object species comprises at least about 50 percent (on a molar basis) of all macromolecular species present. Generally, a substantially pure composition will be understood to comprise more than about 75% of all macromolecular species present in the composition, and in alternate embodiments may comprise at least about 80%, at least about 85%, at least about 90%, at least about 91%, at least about 92%, at least about 93%, at least about 94%, at least about 95%, at least about 96%, at least about 97%, at least about 98%, or at least about 99% of the object species. In one embodiment, the object species is purified to essential homogeneity, wherein the composition consists substantially of a single macromolecular species. The term "pure" or "substantially pure" also refers to preparations where the object species is at least 60% (w/w) pure, or at least 70% (w/w) pure; or at least 75% (w/w) pure; or at least 80% (w/w) pure; or at least 85% (w/w) pure, or at least 90% (w/w) pure, or at least 91% (w/w) pure, or at least 92% (w/w) pure, or at least 93% (w/w) pure, or at least 94% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

As used herein, the term "subject" or "patient" refers to a warm blooded animal, particularly a mammal, which is afflicted with a condition or disease to be treated according to the presently disclosed treatment embodiments. It is understood that guinea pigs, dogs, cats, rats, mice, horses, goats, cattle, sheep, zoo animals, livestock, monkeys, primates, humans, and any other animals with mammary tissue are examples of animals within the scope of the meaning of the term.

"Treatment" refers to therapeutic treatments. "Prevention" refers to prophylactic or preventative treatment measures. The term "treating" refers to administering the composition to a patient or subject for therapeutic purposes. "Treatment" refers to both therapeutic treatment and prophylactic or preventative measures. Those in need of treatment include, but are not limited to, individuals already having a particular condition or disease as well as individuals who are at risk of acquiring a particular condition or disease (e.g., those needing prophylactic/preventative measures). The term "treating" refers to administering an agent to a subject for therapeutic and/or prophylactic/preventative purposes. The term "treat" or "treatment" encompasses the complete range of therapeutically positive effects associated with pharmaceutical medication including reduction of, alleviation of and relief from the symptoms or illness, which affect the subject.

A "therapeutic composition" or "pharmaceutical composition" refers to an agent that may be administered in vivo to bring about a therapeutic and/or prophylactic/preventative effect in accordance with the presently disclosed and claimed inventive concept(s).

Administering a therapeutically effective amount or prophylactically effective amount is intended to provide a therapeutic benefit in the treatment, reduction in occurrence, prevention, or management of a disease and/or disorder. The specific amount that is therapeutically effective can be readily determined by the ordinary medical practitioner, and can vary depending on factors known in the art, such as the type of disease/disorder, the patient's history and age, the stage of disease/disorder, and the co-administration of other agents.

A "disorder" is any condition that would benefit from treatment with the protein-carbon nanotube complex of the presently disclosed and claimed inventiveconcept(s). This includes chronic and acute disorders or diseases including those pathological conditions which predispose the mammal to the disorder in question.

The term "effective amount" or "therapeutically-effective amount" refers to an amount of a biologically active molecule or complex or derivative thereof sufficient to exhibit a detectable therapeutic effect without undue adverse side effects (such as toxicity, irritation and allergic response) commensurate with a reasonable benefit/risk ratio when used in the manner of the presently disclosed and claimed inventive concept(s). The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease in conjunction with the conjugates of the presently disclosed and claimed inventive concept(s). This concurrent therapy can be sequential therapy where the patient is treated first with one drug and then the other, or the two drugs are given simultaneously.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The terms "administration" and "administering", as used herein will be understood to include all routes of administration known in the art, including but not limited to, oral, topical, transdermal, parenteral, subcutaneous, intranasal, mucosal, intramuscular, intraperitoneal, intravitreal and intravenous routes, including both local and systemic applications. In addition, the compositions of the presently disclosed and claimed inventive concept(s) (and/or the methods of administration of same) may be designed to provide delayed, controlled or sustained release using formulation techniques which are well known in the art.

By "polypeptide" or "protein" or "peptide" is meant a molecule comprising a series of amino acids linked through amide linkages along the alpha carbon backbone. Modifications of the peptide side chains may be present, along with glycosylations, hydroxylations and the like. Additionally, other nonpeptide molecules, including lipids and small molecule agents, may be attached to the polypeptide.

As is well known to persons of ordinary skill in the art, given an amino acid or an amino acid sequence of a protein, polypeptide, or peptide, one can make substitutions and changes to the certain amino acids without substantially changing the functionality of the protein, polypeptide, or peptide. As such, the presently disclosed and claimed inventive concept(s) should not be regarded as being solely limited to the sequences of specific proteins, polypeptides, or peptides disclosed herein. For example, standardized and accepted functionally equivalent amino acid substitutions which may be used are presented in Table 1.

TABLE 1

| Amino Acid Group | Conservative and Semi-Conservative Substitutions |
|---|---|
| Nonpolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

The term "receptor" as used herein will be understood to include any peptide, protein, polypeptide, glycoprotein, polycarbohydrate, or lipid that is uniquely expressed or overexpressed on the surface of a cell such as a cancer cell or vasculature of a tumor and is exposed on the surface of such cells in a manner that will allow interaction with a circulating targeting agent, such as the conjugate described herein.

As used herein, a "CNT-conjugate" or "CNT-complex" or "protein-CNT complex" refers to a compound that contains at least one receptor-binding linking protein, polypeptide, or peptide and at least one carbon nanotube molecule (such as a SWNT) which are coupled, adsorbed or otherwise linked to one another directly or via a linking moiety. The term "protein-carbon nanotube complex" is also intended to be used interchangeably with "protein-CNT complex" where used herein.

Further as used herein, a "SWNT-conjugate" or "SWNT-complex" or "protein-SWNT complex" refers to a compound that contains at least one receptor-binding linking protein or peptide and at least one SWNT which are coupled, adsorbed or otherwise linked to one another directly or via a linking moiety.

Turning now to the various embodiments of the presently disclosed and claimed inventive concept(s), methods and compositions for detecting and destroying cancer tumors or cancer cells, or other cells having specific receptors or binding sites contemplated herein, are provided. The methods are based on administering to a subject a composition comprising a linking protein or peptide such as, but not limited to, annexin V, which is attached to or physically associated with a carbon nanotube (CNT) such as a single-walled carbon nanotube (SWNT), e.g., a semiconducting SWNT, a double-walled carbon nanotube (DWNT) or a multi-walled carbon nanotube (MWNT) to form a protein-CNT complex or peptide-CNT complex. Where used herein the term "protein-CNT complex" is also intended to include the term peptide-CNT complex unless otherwise noted. Said linking protein or peptide can selectively bind to cancerous cells (especially tumor vasculature endothelial cells) rather than to healthy cells by binding to phosphatidylserine (PS), phosphatidylinositol (PI), phosphatidic acid (PA) or phosphatidylglycerol (PG), or other cancer specific receptors or binding sites specifically expressed, over-expressed, or preferentially expressed on the outer surfaces of cancer cells. Irradiation of the CNTs with specific wavelengths can be used to detect and destroy those cancer cells to which the CNTs are bound via the linking protein or peptide. In a further embodiment, an immunostimulant is also administered to the patient either before, with, during, or after the administration and/or irradiation of the protein-CNT complex, as described in more detail below.

In certain embodiments, the presently disclosed and claimed inventive concept(s) include use of protein-carbon nanotube complexes (including for example protein-SWNT complexes, and more particularly annexin V-SWNT complex) to treat various cancers, including but not limited to, lung and bronchial cancer, pancreatic cancer, brain cancer, breast cancer, thyroid cancer, bladder cancer, skin cancer including melanoma, prostate cancer, renal cell cancer, colon cancer, rectal cancer, ovarian cancer, uterine cancer, leukemia, and lymphoma or any other cancer characterized by specific surface receptors or binding sites.

Lung cancer is by far the most common cause of cancer related mortality in the United States (20). The overall 5-year survival rate for patients with pancreatic cancer ranges from 1% to less than 5%, and there has been little improvement in survival rates in the last 20 years (21). Malignant glioma brain cancer occurs more frequently than other types of primary central nervous system tumors, having a combined incidence of 5-9/100,000 population (22). Currently, the most effective treatment of glioma is a combination of temozolomide chemotherapy and radiotherapy; however, the median survival with this treatment is still only 13 months (23).

As explained herein, the treatment disclosed herein using protein-CNT complexes such as annexin V-CNT complex is designed to be selective for cancer tumors, so that normal tissue will be substantially unaffected, thus minimizing or eliminating significant side effects. The use of annexins, such as annexin V, as an agent for targeting CNTs, and particularly SWNTs, to the tumor vasculature has the great advantage that delivery is necessary only to the bloodstream of cancer patients and not directly to the surface of all cells of the tumor, thus overcoming a major disadvantage of other protein-based therapeutics for cancer treatment. Because preferably delivery is via the bloodstream, multiple cancer tumors (e.g., metastatic cancer) can be treated simultaneously. The impact of the presently disclosed and claimed inventive concept(s) will result in great benefits to society, for example in that cancers can be treated more rapidly and with much less suffering to patients, and many patients will thus live much longer after treatment compared to current treatments available.

Where used herein, the term "annexin" refers to any of annexins 1-11 and 13, which are more particularly designated as annexins A1, A2, A3, A4, A5, A6, A7, A8, A9, A10, A11, and A13. Annexin V where used herein refers to Annexin A5, for example. The annexins contemplated herein further include non-human cognate orthologs of A1-A11 and A13 for non-human vertebrates, including but not limited to non-human primates, dogs, cats, horses, livestock animals and zoo animals, which may be used for treatment in said non-human mammals in the methods disclosed herein. The annexins contemplated for use herein are discussed in further detail in V. Gerke and S. E. Moss (Gerke, V. and S. E. Moss, "Annexins: From Structure to Function" *Physiol. Rev.* 82: 331-371, 2002), the entirety of which is expressly incorporated by reference herein in its entirety.

Anionic phospholipids are largely absent from the surfaces of resting mammalian cells under normal conditions. PS is the most abundant anionic phospholipid of the plasma membrane and is tightly segregated to the internal side of the plasma membrane in most cell types. Recently, it has been discovered that PS is expressed on the outside surface of the endothelial cells that line the blood vessels in tumors in mice but is not expressed on the outside surface of the vascular endothelium in normal organs. In addition, anionic phospholipids have been shown to be expressed on the outside surface of cancer cells.

The tumor vasculature is increasingly recognized as a target for cancer therapy. Angiogenesis, the formation of new capillaries from existing blood vessels, is essential for the growth of solid tumors beyond 3 mm in size. Damage to the endothelial cells that line the blood vessels results in the induction of the coagulation cascade, causing intratumoral vessel occlusion and subsequent tumor necrosis. Targeting the tumor vasculature has the advantage that the delivery vehicle, once in the bloodstream, has direct access to the target endothelial cells. Other advantages of targeting the tumor vasculature rather than the tumor cells themselves include a potentiation effect, because one blood vessel nourishes hundreds of tumor cells. However, prior to the present disclosure, to the best of the inventors' knowledge, there have been no studies reported of targeting carbon nanotubes to the tumor vasculature.

Human annexin V, one protein disclosed for use herein, and which is a member of the annexin family of $Ca^{2+}$-dependent anionic phospholipid binding proteins (others are noted above), is operatively attached to or otherwise physically associated with (e.g., by adsorption, complication or conjugation) to SWNTs for targeting the tumor vasculature endothelial cells, is a member of a class of widely distributed proteins which bind to anionic phospholipids and membranes in a $Ca^{2+}$ dependent manner. Annexin V is a monomeric protein, which has been crystallized and shown to consist of four tandem repeats of similar structure. Structural evidence shows that the N terminus of annexin V is located at the surface of the protein and faces away from the membrane-binding side of the molecule. It was found that the attachment of prourokinase at the N terminus of annexin V did not alter its affinity for cell membranes in which PS was exposed on the membrane surface, which is consistent with the previous structural evidence.

Annexin V and other annexins bind with very high affinity to PS-containing phospholipid bilayers. In one embodiment of the presently disclosed and claimed inventive concept(s), one of annexins A1-A11 and A13 such as, annexin A5 (annexin V), is adsorbed, conjugated or complexed (i.e., physically associated) to SWNTs. The annexin V-SWNT complexes are then injected into the bloodstream of a subject where they selectively bind to the vasculature in a tumor or tumor cells associated therewith. Alternatively, the annexin V-SWNT complex is injected directly into the tumor in the subject and bind selectively to cancer cells. Annexin V may be obtained as described in U.S. Published Application 2006/0258584.

Examples of other PS-binding proteins that can be used instead of those of the Annexin family include, but are not limited to, lactadherin, domains found in proteins known to bind PS, such as Factor V/Va, Factor X/Xa, Factor II/IIa, Factor VII/VIIa, Factor IX/IXa, Factor VIII/VIIIa, Spectrin, Class B Scavenger receptor type I, Protein Kinase C, and proteins containing the C2 domains of protein kinase C (this includes synaptotagmins), Rabphilin family members, the PS receptor, endothelial lectin-like OxLDL receptor-1 (LOX-1), antibodies to PS, phosphatidylserine decarboxylase, MARCKS (myristoylated, alanine-rich protein kinase C substrate), PS-p68, Myosin, Erythrocyte protein 4.1, hemoglobin, Calponin family members, S100A, S100B, calcyclin-binding protein family members, milk membrane-glycoprotein, MFG-E8 (milk fat globule-EGF factor 8), and other PS-binding motifs known to those of ordinary skill in the art.

Other linking proteins or peptides which may be used in combination with carbon nanotubes such as SWNTs as contemplated herein include, but are not limited to, RGD-motif peptides (Receptor: integrins alpha-v-beta 3 and alpha-v-beta 5); NGR-motif peptides (Receptor: aminopeptidase N, also known as CD13); F3, a 34-amino acid basic peptide from HMGN2 (Receptor: cell surface nucleolin); HWGF-motif (SEQ ID NO:1) peptides (selective inhibitors of matrix metalloproteinase-2 and matrix metalloproteinase-9, also know as gelatinase A and gelatinase B); the synthetic peptide CTTHWGFTLC (SEQ ID NO:2) (which targets angiogenic blood vessels, inhibits the migration of human endothelial cells and tumor cells, and also prevents tumor growth and invasion in animal models and improves survival of mice bearing human tumors); and amino-terminal fragment (ATF) of urokinase (which binds to the urokinase receptor, but, unlike full length urokinase, is not internalized).

The linking protein may be a phosphatidylserine-specific or other anionic phospholipid-specific monoclonal antibody to which the SWNT is complexed, conjugated or adsorbed or otherwise physically associated with methods known to those of ordinary skill in the art, for example using functionalized SWNTs. Examples of PS-specific monoclonal antibodies include, but are not limited to, those described in U.S. Pat. Nos. 6,406,693; 6,818,213; 6,312,694; 6,783,760; 7,247,303; and PCT application WO2004/006847. The linking protein or peptide to which the SWNT is associated may be a non-PS-binding moiety which binds to another tumor-specific feature, such as but not limited to those described in U.S. Pat. Nos. 6,451,312; 6,093,399; 6,004,555; and 6,051, 230. The presently disclosed and claimed inventive concept(s) include, in other embodiments, other tumor/cancer-specific external receptors other than aminophospholipids as targets for the protein-carbon nanotube complexes, including for example, those described in U.S. Pat. Nos. 6,818,213; 6,783,760; 6,451,312; and 6,406,693.

After treatment with the protein-CNT complex or peptide-CNT complex of the presently disclosed and claimed inventive concept(s), the cancer cells or tumor having the CNTs bound thereto are then selectively exposed to appropriate wavelengths of electromagnetic radiation, for example, radio frequency radiation, near-infrared (NIR) radiation, visible light, or UV radiation. The energy level of NIR radiation can be adjusted to give excessive local heating of CNTs such as SWNTs but not otherwise affect biological systems which are not associated to the CNTs. This excessive local heating of the CNTs bound to the surface of endothelial cells of the tumor vasculature or to surfaces of the cancer cells leads to the destruction of the tumor vasculature or of the cancer cells and thus to the death or inhibition of growth of the tumor or cancer cells. Without wishing to be held to theory, it is believed in one embodiment that the killing of the tumor is by a combination of heating and cutting off the tumor's blood supply. In order to avoid damage to normal blood vessels, it is advantageous to delay the NIR treatment (or treatment with other wavelengths) until there is clearing of free CNTs from the bloodstream such that substantially the only CNTs in the body are those bound to the tumor vasculature or cancerous cells. The free CNTs should clear within a matter of hours after administration. For example, in a recent study with rabbits, SWNTs were injected into the bloodstream, and the SWNT concentration decreased exponentially with a half-life of 1.0±0.1 hour. No adverse effects from low-level SWNT exposure could be detected from behavior or pathological examination.

The presently disclosed and claimed inventive concept(s) in certain embodiments are directed to a protein-SWNT or peptide-SWNT compound (also referred to herein as a protein-SWNT complex) that specifically targets a SWNT to the surface of cancer cells. The complex includes the SWNT and a ligand that binds to a receptor found on cancer cells. In one embodiment the SWNT is a semiconducting SWNT. The receptor may be solely expressed on cancer cells or may be overexpressed on cancer cells, such that the SWNT is selectively delivered to the cancer cells.

The ligand of the protein-CNT complex (e.g. protein-SWNT complex) of the presently disclosed and claimed inventive concept(s) may be any protein, peptide or composition which binds to the receptor or targeting ligand. When the ligand is a protein, the ligand may contain the entire protein that binds to the desired receptor, or may contain only a portion of the protein. For example, it may be desirable to remove a portion of the protein that has an undesirable biological activity, or it may be desirable to remove a portion of the protein to enable attachment of the CNT. The only requirement when a portion of the protein is present as the ligand in the complex is that the portion of the protein substantially retains the protein's receptor binding activity. The terms "portion" and "fragment" are used herein interchangeably.

Likewise, the protein-CNT complex may contain a variant of the linking protein. For example, in certain embodiments, a portion of the ligand that has an undesirable biological activity is modified, or a portion of the ligand may be modified to enable attachment of the anticancer agent. The only requirement when a variant of the ligand is present in the complex is that the ligand variant substantially retains the ligand's receptor binding activity. Also, sequences may be added to or inserted within the ligand during modification, as long as the modified ligand substantially retains the ligand's receptor binding activity. Therefore, it is to be understood that the term "ligand variant" includes both substitutions (including but not limited to conservative and semi-conservative substitutions) as well as additions and insertions to the native ligand's sequence that do not substantially affect the ligand's receptor binding activity. Such variations may occur at the nucleic acid level during construction of the construct from which the complex is expressed, or the variations may be produced by other posttranscriptional or posttranslational means known to those or ordinary skill in the art, including but not limited to, mutations and chemical modifications.

Examples of receptors that may be targeted by protein-SWNT complexes in accordance with the presently disclosed and claimed inventive concept(s) include, but are not limited to, urokinase receptor, epidermal growth factor (EGF) receptor, insulin-like growth factor receptor, interleukin-4 (IL-4) receptor, interleukin-6 (IL-6) receptor, keratinocyte growth factor (KGF) receptor, platelet-derived growth factor (PDGF) receptor, fibroblast growth factor (FGF) receptor, laminin receptor, vascular endothelial growth factor (VEGF) receptor, transferrin receptor, fibronectin, and the like, as well as portions thereof and variants thereof that substantially maintain the ability to bind to at least one receptor.

In alternative embodiments, the protein-CNT complex may contain all or a portion or variant of one of the following ligands to target the protein-CNT complex to one or more of the above receptors: urokinase, epidermal growth factor (EGF), transforming growth factor-alpha (TGFα), insulin-like growth factor, interleukin-4 (IL-4), interleukin-6 (IL-6), platelet-derived growth factor (PDGF), fibroblast growth factor (FGF), laminin, vascular endothelial growth factor (VEGF), antibodies or antibody fragments (such as but not limited to antibodies to the transferrin receptor or the ED-B domain of fibronectin), and the like. The structure and properties of some of the above-listed growth factors are very similar, and therefore one growth factor may be utilized to target another receptor (for example, TGFα may be utilized to bind to the EGF receptor).

The modification of one of the receptor-binding ligands described herein above to provide a fragment or variant thereof that substantially maintains the receptor-binding ability of the native receptor-binding ligand is fully within the skill of a person in the art and therefore is also within the scope of the presently disclosed and claimed inventive concept(s). The term "substantially maintains the receptor-binding ability of the native receptor-binding ligand" means that the protein fragment or variant maintains at least 50% of the native ligand's receptor-binding ability, and particularly at least 75% of the native ligand's receptor-binding ability, and more particularly at least 90% of the native ligand's receptor-binding ability.

The protein-CNT complex of the presently disclosed and claimed inventive concept(s) may be administered to a subject by any methods known in the art, including but not limited to, oral, topical, transdermal, parenteral, subcutaneous, intranasal, intramuscular and intravenous routes, including both local and systemic applications, and other methods disclosed herein. In addition, the complexes of the presently disclosed and claimed inventive concept(s) may be designed to provide delayed or controlled release using formulation techniques which are well known in the art.

The presently disclosed and claimed inventive concept(s) also include, in certain embodiments, a pharmaceutical composition comprising a therapeutically effective amount of the protein-CNT complex described herein above in combination with a pharmaceutically acceptable carrier or vehicle. As used herein, a "pharmaceutically acceptable carrier or vehicle" is a pharmaceutically acceptable solvent, suspending agent or vehicle for delivering the complexes of the presently disclosed and claimed inventive concept(s) to the human or animal. The carrier may be liquid or solid and is selected with the planned manner of administration in mind. Examples of pharmaceutically acceptable carriers that may be utilized in accordance with the presently disclosed and claimed inventive concept(s) include, but are not limited to, PEG, liposomes, ethanol, DMSO, aqueous buffers, oils, and combinations thereof.

The protein-CNT complex of the presently disclosed and claimed inventive concept(s) differ in several ways in comparison to methodologies of the prior art. First, since the CNT is being targeted to cells that it is intended to kill, the dosages of the protein-CNT complex containing the CNT will be substantially reduced, versus other conventional cancer treatments such as chemotherapy. Second, since CNTs themselves are not toxic, they will not have the toxic side effects of typical of chemotherapies.

Single-Walled Carbon Nanotubes

In some embodiments, the CNTs used herein comprise semiconducting SWNTs. The SWNTs may be produced, for example, from cobalt-molybdenum catalysts which produce SWNTs of high specificity as opposed to other forms of carbon by using patented proprietary methods of catalytic CO disproportionation (CoMoCAT® process, SouthWest NanoTechnologies Inc., Norman, Okla.). For example, in the CoMoCAT® process, the (n,m) distribution of the SWNT product can be reproducibly altered by varying the reaction temperature, the gaseous feed, or the cluster surface morphology. This control of (n,m) structure provides a remarkable tool for tailoring specific nanotubes without the need of sophisticated post-growth separation methods. The value of a high selectivity to a specific (n,m) nanotube resides in the unique optical response of each (n,m) structure. For example, the (6,5) SWNTs produced using the CoMoCAT® process at 750° C., have sharp absorption lines at 975 nm and 565 nm. The SWNTs can effectively absorb radiation at these two specified wavelengths or can emit radiation at the wavelength of lower energy (975 nm) via photoluminescence. Accordingly, once in contact with the targeted cell, the nanotubes can act as fluorescent markers emitting at 565 nm, or as radiation absorbing targets at either 975 nm (near infrared) or 565 nm (visible). Other SWNTs which may be used in various embodiments of the presently disclosed and claimed inventive concept(s) have absorption/emission wavelengths as shown in Table 4 below.

One benefit of using near-infrared radiation to irradiate the localized SWNTs of the compounds of the presently disclosed and claimed inventive concept(s) is that the human tissue and blood are almost completely transparent in this spectral region as long as the energy level of near-infrared radiation is kept sufficiently low. As a result, it is very convenient for selectively heating those cells (tumor cells or cells in tumor vasculature) to which the SWNTs are bound, while leaving the healthy cells and tissues substantially unaffected.

This relative transparency also allows for detection of the location of tumors or cancer cells via detection of emission wavelengths or fluorescence of the excited SWNTs. By using SWNTs of different (n,m) structure in the single therapeutic composition (or single therapeutic treatment protocol) one can have available samples that absorb and emit at different wavelengths thereby allowing determination of locations of tumors, localized cancer cells, or metastatic tumors or cancer cells in the body. However, it may also be desirable to use a composition which is enriched in a single SWNT structure such as (6,5) or (7,6) or others. As used herein enriched means at least 20%, at least 25%, at least 40%, at least 50%, at least 60%, at least 75%, or more of the SWNTs in the composition comprise a single semiconducting (n,m) structure such as (6,5) or (7,6). In other embodiments, the semiconducting (n,m) structures include for example (7,5), (8,6), (8,7), (9,7) and (9,8).

As noted above, SWNTs can be produced using CoMoCat® methods such as described in U.S. Published Patent Application 2004/0131532, or in U.S. Ser. No. 12/111,617, filed Apr. 29, 2008, and entitled "MICROSTRUCTURED CATALYSTS AND METHODS OF USE FOR PRODUCING CARBON NANOTUBES", the entireties of which are hereby expressly incorporated herein by reference. These SWNTs, as noted, have very narrow diameter and chirality distributions and are produced by CO disproportionation on bimetallic Co—Mo catalysts supported on silica. In one embodiment, using feeds of pure CO or CO with 1% $H_2$ at 750° C., SWNTs with strong absorption at 980 nm, 1030 nm, and 1120 nm, for example, are produced. Since the depth of penetration of light into tissue increases as the wavelength increases, these SWNTs can be used in PDT because the wavelengths that give maximum absorption are considerably higher than have been used clinically for cancer treatment previously (i.e., 600-700 nm).

SWNTs used herein can be functionalized (derivatized) if desired, for example by adding carboxylic acid groups (—COOH) on the ends of the SWNTs, using, for example, the following exemplary treatment with sulfuric and nitric acids: (1) mix 30 mg SWNTs and 30 ml acid (e.g., $H_2SO_4$:$HNO_3$=1:3) and 30 ml DI water; (2) Sonicate for 24 hours; and (3) filter and wash until the pH is about 6.

Functionalization is one method of treating the SWNTs to enable them to remain as a stable suspension in water, which is useful in further functionalizing them with annexin V. SWNTs produced by this procedure also retain their original optical absorption properties.

As indicated herein, SWNTs are used as an element in PDT that leads to destruction of the tumor vasculature. Extensive death of HeLa cancer cells in cell culture has been found after treatment with SWNTs functionalized with folate and then exposure to near-infrared (NIR) light at 808 nm for 2 minutes at a power level of 1.4 W/cm². Extensive local heating of SWNTs caused by continuous NIR absorption was the most likely reason for cell death, suggesting that the SWNTs acted as tiny NIR heaters or antennas. In contrast, the same cells with no SWNTs present survived continuous treatment at a power of 3.5 W/cm², which shows the high transparency of biosystems to NIR light.

Compared to the previously available photosensitizers, the use in PDT in certain embodiments described herein of SWNTs which are operatively associated with (e.g., conjugated, adsorbed or complexed to) a protein or peptide such as annexin V (or other linking protein or peptide) result in at least the following: (1) the protein/peptide-SWNT complexes enable deeper penetration of the light into the tissue, since the wavelength of the light can be much higher (e.g., over 1100 nm, depending on the SWNTs used); (2) instead of being distributed throughout the body, the protein/peptide-SWNT complexes are specifically targeted to the tumor or tumor vasculature, which greatly reduces the potential toxicity to the patient; and (3) the protein/peptide-SWNT complexes completely avoid the problem of skin photosensitivity.

Adsorption or Complexation of Protein or Peptide to SWNTs

In certain embodiments, the linking protein or peptide, e.g., annexin V protein, may be operatively attached to the CNTs by adsorption or complexing. It is useful to preserve the optical absorption and photoluminescence of CNTs in the range of NIR, since biological systems exhibit a significantly deep penetrability but very low absorption of NIR photons in the range of 700-1,100 nm. In one embodiment the CNTs contemplated for use herein are SWNTs which are enriched in the (6,5) type (e.g., in one embodiment at least 50% of the SWNTs are (6,5)). SWNTs of (6,5) structure exhibit a sharp absorption as well as fluorescence band at around 980 nm.

In one embodiment, CNTs are first completely suspended in a solution with a low concentration of sodium cholate, a bile salt which acts as a surfactant. Subsequently, the protein or peptide to be adsorbed is added to the suspension, wherein the protein is adsorbed to the CNTs, and the sodium cholate is removed by dialysis leaving the protein-CNT complex. In one experiment for example, it was demonstrated that a model protein, horseradish peroxidase, adsorbs to CNTs using the sodium cholate suspension-dialysis method and enables the CNTs to be stably suspended. This adsorption led to a nearly complete retention of enzymatic activity of horseradish peroxidase and also retention of a substantial fraction of the NIR absorption at 980 nm.

A suspension of single-wall carbon nanotubes (SWNTs) can be prepared, for example, by dispersing purified SWNTs (as previously described) in a 2 wt. % aqueous solution of sodium cholate (Sigma-Aldrich). The heterogeneous mixture of SWNTs and aqueous solution are horn sonicated for e.g., 1 hour using a homogenizer (e.g., set at 22% amplitude, Cole-Parmer model CPX750) resulting in a dark black liquid. This suspension of SWNTs can then be centrifuged at 30,100×g for 1 hour.

The linking protein can be adsorbed onto the SWNTs by using, for example, the following procedure at 4° C.: Sodium phosphate is added to the SWNT suspension to give a concentration of 20 mM. To this solution 20 mg of protein is added, and dialysis using a 10 kDa dialysis membrane (Spectrum Laboratories) is carried out with sodium phosphate buffer solution at pH 7.4 for 12 hours to remove sodium cholate. The resulting solution is transferred to a 100 kDa dialysis membrane (Spectrum Laboratories, Ranch Dominguez, Calif.) and dialyzed against sodium phosphate buffer at pH 7.4 to remove unabsorbed protein, with a change of the buffer at 2, 4, 16, and 24 hours from the start of dialysis. The final suspension is centrifuged at 29,600×g for 1 hour, and the supernatant is retained.

A stable protein-SWNT complex is obtained after the final centrifugation of the preparation process and retains a substantial fraction of NIR absorption at 980 nm. The protein-SWNT complex can then be used therapeutically as discussed elsewhere herein.

Other methods that can be used to adsorb proteins on SWNTs include but are not limited to organic solvent displacement method and the aqueous sonication method, for example or other methods described below.

In an alternative embodiment of the presently disclosed and claimed inventive concept(s), a substantially inert macromolecular intermediate linking moiety such as a polymer or protein (e.g., a polyalkylene glycol such as polyethylene glycol (PEG), or human serum albumin, carboxymethylcellulose (CMC), hydroxymethylcellulose (HEC) or hydroxylpropylcellulose (HPC) or other inert polymer) can be adsorbed to the CNTs (thereby improving solubility of the CNTs in aqueous solution). The intermediate linking moiety which is adsorbed to the CNT can then be covalently attached to the linking protein or peptide (e.g., annexin V), for example by linking a functional group on the intermediate linking moiety to an amino group or side group of the linking peptide or protein. The chemistry for peptide and protein PEGylation for example is well developed and known to those having ordinary skill in the art.

In one embodiment for example, a phospholipid-PEG-aldehyde (or other inert carrier contemplated herein) is adsorbed to the CNTs giving a dispersion of substantially nonaggregated CNTs (e.g. SWNTs). The PL-PEG-CNT is then reacted with the linking protein or peptide (e.g., annexin V) wherein the aldehyde group of the PEG joins to the N-terminal amino group of the linking protein or peptide (or other exposed amine group on another amino acid of the linking protein or peptide).

PEG molecules can be modified by functional groups and the amino terminal end of the linking protein or peptide, or cysteine residue if present, or other linking amino acid therein can be linked thereto, wherein the PEG molecule can carry one or more linking proteins or peptides.

By "polyethylene glycol" or "PEG" is also meant any other polyalkylene glycol compound or a derivative thereof, with or without coupling agents or derivatization with coupling or activating moieties (e.g., with thiol, triflate, tresylate, azirdine, oxirane, or particularly with a maleimide moiety). Compounds such as maleimido monomethoxy PEG are exemplary or activated PEG compounds of the presently disclosed and claimed inventive concept(s). In non-limiting embodiments, the protein or peptide is linked to the CNT via a DSPE-PEG-maleimide linker or via a Fmoc-NH-PEG-NHS linker (see U.S. Provisional Ser. No. 61/734,802). Other polyalkylene glycol compounds, such as polypropylene glycol, may be used in the presently disclosed and claimed inventive concept(s). Other appropriate polymer conjugates include, but are not limited to, non-polypeptide polymers, charged or neutral polymers of the following types: dextran, colominic acids or other carbohydrate based polymers, biotin derivatives and dendrimers, for example. The term PEG is also meant to include other polymers of the class polyalkylene oxides.

The PEG can be linked to any N-terminal amino acid of the linking protein or peptide, and/or can be linked to an amino acid residue downstream of the N-terminal amino acid, such as lysine, histidine, tryptophan, aspartic acid, glutamic acid, serine, threonine, methionine, tyrosine, and cysteine, for example or other such linkable amino acids known to those of skill in the art. Cysteine-PEGylated linking proteins or peptides, for example, are created by attaching polyethylene glycol to a thio group on a cysteine residue of the linking protein or peptide.

The PEG moiety attached to the linking protein or peptide may range in molecular weight, for example, from about 200 to 20,000 MW.

The linking proteins and peptides contemplated herein can be adsorbed or linked to PEG molecules or other suitable polymers (as noted above) using techniques shown, for example (but not limited to), in U.S. Pat. Nos. 4,179,337; 5,382,657; 5,972,885; 6,177,087; 6,165,509; 5,766,897; and 6,217,869; and Published U.S. Application 2006/0275371; the specifications and drawings each of which are hereby expressly incorporated by reference herein in its entirety.

EXAMPLES

Examples are provided hereinbelow. However, the presently disclosed and claimed inventive concept(s) are to be understood to not be limited in their application to the specific experimentation, results and laboratory procedures described herein. Rather, the Examples are simply provided as several of various embodiments and are meant to be exemplary, not exhaustive.

Example 1

In one embodiment, a suspension of SWNTs was made by dispersing 3 mg of pristine nanotubes (CoMoCAT® sample supplied by SouthWest Nanotechnologies, Norman, Okla.) and 140 mg of carboxymethylcellulose (50 kDa) in 7 g of deionized water. This mixture was horn sonicated for 30 minutes using a homogenizer (22% amplitude, Cole-Parmer model CPX750) resulting in a dark black liquid. This suspension of SWNTs was then centrifuged at 30,000×g for 30 minutes, and the supernatant was saved. This supernatant was transferred to a 100 kDa dialysis membrane (Spectrum Laboratories, Rancho Dominguez, Calif.) and then dialyzed against 2 liters of an aqueous solution with 0.5 M sodium chloride for 8 hours at 4° C.

EDC (1-ethyl-3-[3-dimethylaminopropyl]carbodiimide hydrochloride 1-ethyl-3) (Pierce, Rockford, Ill.) was used to link the carboxyl groups on CMC to the amino groups on annexin V (or could be used with any linking protein or peptide contemplated herein). EDC is a carboxyl and amine-reactive zero-length cross linker. EDC reacts with a carboxyl group first and forms an amine-reactive O-acylisourea intermediate that quickly reacts with an amino group to form an amide bond and release of an isourea by-product. The intermediate is unstable in aqueous solutions; and therefore, when performing two-step conjugation procedures, N-hydroxysuccinimide (NHS) is required for stabilization. Failure to react with an amine will result in hydrolysis of the intermediate, regeneration of the carboxyl, and release of an N-substitute urea. The following procedure was adapted from a procedure described by Grabarek and Gergely (37) and allows sequential coupling of CMC and a protein without affecting the protein's carboxyls by exposing them to EDC. This procedure requires quenching the first reaction with a thiol-containing compound.

First, EDC and NHS were equilibrated to room temperature. Then 2.8 mg EDC (≈2 mM) and 4.2 mg of NHS were added to the SWNT-CMC suspension and reacted for 15 minutes at room temperature. 9.8 µl of 2-mercaptoethanol (final concentration of 20 mM) was added to quench the EDC. Next, annexin V was added at a concentration of 0.35 mg/ml to the SWNT-CMC suspension, and the solution was allowed to react for 2 hours at room temperature. To quench the reaction, hydroxylamine was added to a final concentration of 10 mM. This method hydrolyzes nonreacted NHS present on SWNT-CMC and results in regeneration of the original carboxyls. Excess reagent was then removed using a dialysis membrane (100 kDa) immersed in 2 liters of sodium phosphate buffer (20 mM, pH 7.4). The buffer was replaced after 4 hours from the beginning of the dialysis, which has a total duration of 8 hours. The solution was centrifuged at 30,000×g for 1 hour, in order to isolate the SWNT-CMC fraction bound to annexin V; the supernatant was retained.

The results are shown in Table 2. These results indicate a relatively high loading of annexin V on the SWNTs (5.2 mg of annexin V per mg of SWNTs).

TABLE 2

| Sample | Protein Concentration | SWNT Concentration | Protein Weight SWNT Weight |
|---|---|---|---|
| SWNT-CMC-annexin V suspension after centrifugation | 74 mg/L | 14.6 mg/L | 5.1 mg/mg |
| Final dialysis solution (2 L) using 100 kDa membrane | 0 mg/L | — | — |

Example 2

Experiments were Conducted to Demonstrate the Binding of SWNT-Annexin V to Human Endothelial Cells In Vitro.

Recombinant annexin V was conjugated to carboxymethylcellulose (CMC) adsorbed to SWNTs using the procedure given above, except the molecular weight of CMC was 30 kDa. Purified recombinant annexin V was labeled with biotin for detection (SureLINK chromophoric biotin labeling kit; KPL, Gaithersburg, Md.) with a 40-molar excess of biotin. Biotin labeling of annexin V has been found previously not to impair the PS-binding of annexin V. The following procedure was used to measure the binding of the SWNT-annexin V (biotinylated) to human endothelial cells in vitro.

Human endothelial cells (American Type Culture Collection, Manassas, Va.) were grown as monolayers in T-75 flasks. Cells ($5 \times 10^4$) were transferred to 24-well plates and grown until ≈70% confluence was reached. PS was exposed on the surface of cells by the addition of hydrogen peroxide (1 mM). Cells were treated with 100 µl of F12K media containing 10% fetal bovine serum and 1 mM of $H_2O_2$ for 1 hour at 37° C. The cells were fixed by adding 100 µl of phosphate buffered saline (PBS) buffer containing 0.25% glutaraldehyde and $Ca^{2+}$ (2 mM). Excess aldehyde groups were quenched by incubating with 50 mM of $NH_4Cl$ (100 µl) diluted in PBS buffer containing $Ca^{2+}$ (2 mM) for 5 minutes. The SWNT-annexin V conjugate was diluted in 0.5% BSA diluted in PBS buffer and $Ca^{2+}$ (2 mM) with an initial concentration of 6700 µM. This concentrated fusion protein solution was serially diluted 2-fold until a final concentration of 6.7 µM. SWNT-CMC-annexin V (300 µl) was added to wells in the increasing concentration of SWNT-CMC-annexin V. For each concentration of SWNT-CMC-annexin V, the experiment was done in duplicate and incubated for 2 hours. Plates were washed with 0.5% BSA diluted in PBS buffer and $Ca^{2+}$ (2 mM) (300 µl). 300 µl of streptadivin-HRP (horseradish peroxidase) (2 µg/ml) was added and incubated for 1 hour at room temperature. The plate was then washed with PBS (300 µl), and the chromogenic substrate O-phenylenediamine (OPD, 300 µl) was added and incubated for 30 minutes. 100 µl of the supernatant was then transferred to 96-well plates, and absorbance was measured at 450 nm (Biotek KC4 microtiter plate reader) using a blank that omits the addition of SWNT-annexin V described above.

Results of Example 2

The covalent linkage of annexin V to CMC adsorbed to SWNTs resulted in a suspension of the annexin V-SWNT complex with a concentration of 163 mg protein per liter. The results of the binding assay for biotinylated annexin V-SWNT complex to human endothelial cells are shown in FIG. 1. The results in FIG. 1 show that the binding to the cells increased as the annexin V-SWNT complex concentration increased. These results are consistent with those obtained previously for the binding of annexin V to PS immobilized on plastic microtiter plates in that the transition from negligible binding to measurable binding also occurred above a concentration of 1000 pM. These results indicate that annexin V is still active and able to bind to PS after being covalently linked to SWNTs. Therefore, these data demonstrate that annexin V-SWNT complex injected into the bloodstream will selectively bind to the tumor vasculature's endothelial cells that have PS exposed on the outside surface. Furthermore, these bound SWNTs when heated by near-infrared light (or other effective wavelength) will lead to death of the endothelial cells and subsequent cutoff of the blood supply to the tumor. The tumor will also be heated, which will cause tumor cells to die.

As noted above, in other embodiments of the presently disclosed and claimed inventive concept(s), the linking protein, or peptide can be covalently linked to the CNT via an intermediate linking moiety, or directly to functionalized CNTs by linking an amino group on the protein or peptide linker to a functional group on the CNT or to a functional group on the intermediate linking moiety. For example, Table 3 shows several potential covalent linkages, and the activation and coupling compound which can be used to form the covalent linkage.

TABLE 3

| Activation and Coupling Method | SWNT or Intermediate Linker Moiety Functional Group | Group on Protein or Peptide |
|---|---|---|
| Glutaraldehyde | Amide | Amino |
| Cyanogen bromide | Hydroxyl | Amino |
| Hydrazine | Amide | Amino |
| Benzoquinone | Hydroxyl | Amino |
| Periodate | Polysaccharide | Amino |
| Trichloro-s-triazine | Hydroxyl | Amino |
| Diazonium | Hydroxyl | Amino |
| Carbonyldiimidazole | Hydroxyl | Tyrosine |
| Tosylates | Hydroxyl | Amino |

Other methods for linking the protein or peptide linker of the presently disclosed and claimed inventive concept(s) to the SWNT (or other carbon nantoube) or the intermediate linking moiety include linkage to anhydride groups on the SWNT or intermediate linking moiety. Alternatively, the linkage may be made to an acyl azide-activated material. The activation of carboxymethylcellulose, for example, is performed first by esterification to yield the methyl ester; this is followed by hydrazinolysis to form the hydrazide. The hydrazide is allowed to react with nitrous acid to form the acyl azide. The acyl azide can then react with the nucleophilic groups, sulfhydryl, amino, or hydroxyl, to yield the thioester, amide, or ester linkage.

In another alternate method, linkage may occur via reaction of amino groups of the protein with the N-hydroxysuccinimide ester of PEG carboxylic acids. This is a common method for coupling PEG to proteins. In another method, 1-pyrenebutanoyl succinimide could be used as an intermediate linking moiety adsorbed to the SWNT then reacted with the protein or peptide linker. Further, PEGs with aldehyde groups could be linked to N-terminal amino groups on the protein or peptide linkers, or another intermediate linking moiety with aldehyde groups could be used. This method is particularly desirable since the linkage is primarily at the N-terminus of the protein or peptide.

Other methods can be used to link the protein or peptide of the presently disclosed and claimed inventive concept(s) directly to the carbon nanotube, or indirectly thereto via the intermediate linking moiety. For example, proteins and peptides can be linked via their reactive residues which include the t-amino of L-lysine (L-Lys) and N-terminus amino group thiol of L-cysteine (L-Cys), carboxyl of L-aspartate (L-Asp) and L-glutamate (L-Glu) and C-terminus carboxyl group, phenolic of L-tyrosine (L-Tyr), guanidino of L-arginine (L-Arg), imidazole of L-histidine (L-H is), disulfide of L-cystine, indole of L-tryptophan (L-Trp), thioether of L-methionine (L-Met), and hydroxyl of L-serine (L-Ser) and L-threonine (L-Thr).

Other cellulose and cellulose derivatives which can be used as intermediate linking moieties in the presently disclosed CNT-protein complexes include for example 4-aminobenzyl-cellulose, aminoethyl cellulose, diethylaminoethyl cellulose, epichlorohydrin triethanolamine-cellulose, oxycellulose, phospho-cellulose, sulfoethyl-cellulose, triethylaminoethyl-cellulose, triazinyl-cellulose, bromacetyl-cellulose, cellulose trans-2,3-carbonate, cellulose imidocarbonate, cellulose azide, cellulose carbonyl, diazocellulose, and isocyanat-cellulose.

In some embodiments, CMC, HEC, or HPC are treated for use as anchors for biological molecules by chemical conversion of all or some of the functional groups on the polymer, and are used to prepare stable CNT suspensions. It is possible to convert the carboxylate functionalities of CMC to aldehydes using a variety of methods. For example the carboxylic acid of CMC can be converted to the acid chloride by thionyl chloride and then reduced to the aldehyde via the Rosenmund catalysts. HEC can be converted to the appropriate functional group by oxidizing a number of the terminal alkyl moieties using pyridinium dichromate in dichloromethane. Hydroxypropyl cellulose (HPC) can be utilized and functionalized in a manner identical to that of HEC.

Other coupling reactions which can be used herein to link the linking groups of proteins to functional groups on the SWNTs or intermediate linking moieties include but are not limited to diazotization, amide (peptide) bond formation, alkylation and arylation, Schiff's base formation, Ugi reaction, amidation reactions, thiol-disulfide interchange reactions, mercury-enzyme interactions, and γ-irradiation induced coupling.

Examples of the reactive groups on the CNTs or intermediate linking moieties which react in these coupling reactions include but are not limited to diazonium salt, acid anhydride, acyl azide, imidocarbonate, isothiocyanate, isocyanate, acyl chloride, cyclic carbonate, O-acylisourea, Woodward's reagent K derivative, δ-fluoramdinitroanilide, triazinyl, oxirane, vinylsulfonyl, vinyl keto, aldehyde, imine, imidoester, cyanide, disulfide residue, mercury derivative, matrix radical, amine, and acylhydrazide.

Further explanation of these linking methods and linking groups can be found in "Covalent and Coordinization Immobilization of Proteins" by J. M. S. Cabral and J. F. Kennedy (in "Protein Immobilization Fundamentals and Applications", ed. R. F. Taylor, (1991), pp. 73-138, Marcel Dekker, Inc.).

Anticancer activity of the presently described therapeutic protein-carbon nanotube complexes can be shown using xenografts in nude mice, including, but not limited the following: one cell line each of lung cancer, pancreatic cancer, and brain cancer cells that are known to be tumorigenic in nude mice. These include, for example, the ATCC cultures A549 human lung adenocarcinoma cells, BxPc-3 human pancreatic adenocarcinoma cells, U-87 human brain glioblastoma cells, and CRL-2539 4T1 metastatic breast cancer cells (e.g., see U.S. Provisional Appln. Ser. No. 61/734,802, expressly incorporated herein by reference). The cancer cells are stably transfected with a β-galactosidase reporter and a quantity of cells (e.g., $5 \times 10^6$ cells) are suspended in Matrigel and injected into the flank of nude mice using the mouse xenograft model. The tumors are grown until they are more than 3 mm, the size above which the growth of new blood vessels is needed for the growth of solid tumors. Before treatment with annexin V-SWNT complexes (or other protein-carbon nanotube complex contemplated herein), tumors are measured by caliper and tumor volumes calculated using the formula: V=(length×width$^2$)/2.

The dosage levels of the annexin V-CNT complex (or other therapeutic protein-CNT or protein-SWNT complex described herein) may range, for example, from 1-5000 mg protein-carbon nanotube complex/kg/day or vehicle (control) by i.v. injection into the subject. A power level of 4.0 W/cm$^2$ is used in one embodiment for the laser treatment, and, in one embodiment the wavelength of about 975-980 nm will be used for the diode laser because this will give the highest absorbance for the SWNTs having (6,5) structure. Laser treatment may be for example from 5 sec to 30 sec, to 1 minute to 2 minutes to 5 minutes to 10 minutes to 20 minutes to 30 minutes per treatment, e.g., one hour after injection. Other power levels may be used as suitable for specific SWNT configurations. The laser treatment time and power density level will depend on the temperature limit to which the tumor tissue can be heated without harming adjacent normal tissue. The temperature rise created by the laser is a direct function of the energy density applied, where energy is power times time. For example, a power density of 4 W/cm$^2$ and a laser treatment time of 5 sec gives an energy density of 4 W/cm$^2 \times 5$ sec=20 W-sec/cm$^2$=20 J/cm$^2$. Other power levels may be used as suitable for specific CNT or SWNT configurations. The power density can be used over the range of 1-100 W/cm$^2$, with the laser treatment time adjusted to the temperature limit desired.

As indicated herein, SWNTs having different (n,m) structures absorb and emit at different wavelengths and can be used herein to form other protein-SWNT compositions. SWNTs absorb in S11 and S22 and emit in S11. S11 and S22 refer to the electronic transitions between occupied and unoccupied levels in semiconducting nanotubes, associated with the first (S11) and second (S22) pairs of the van Hove singularities. Table 4 shows optional emission/absorption wavelengths that can be used in embodiments of protein-SWNT complexes of the presently disclosed and claimed inventive concept(s). Wavelengths ±5 nm those of Table 4 may be used for the particular (n,m) structure. Additionally wavelengths ±10 nm, ±15 nm, ±20 nm, ±25 nm, ±30 nm, ±35 nm, ±40 nm, ±45 nm, ±50 nm, ±55 nm, ±60 nm, ±65 nm, ±70 nm, ±75 nm, ±80 nm, ±85 nm, ±90 nm, ±95 nm, ±100 nm of each of those listed in Table 4 may be used. Other wavelengths not shown in Table 4 may also be used.

Figure 2:
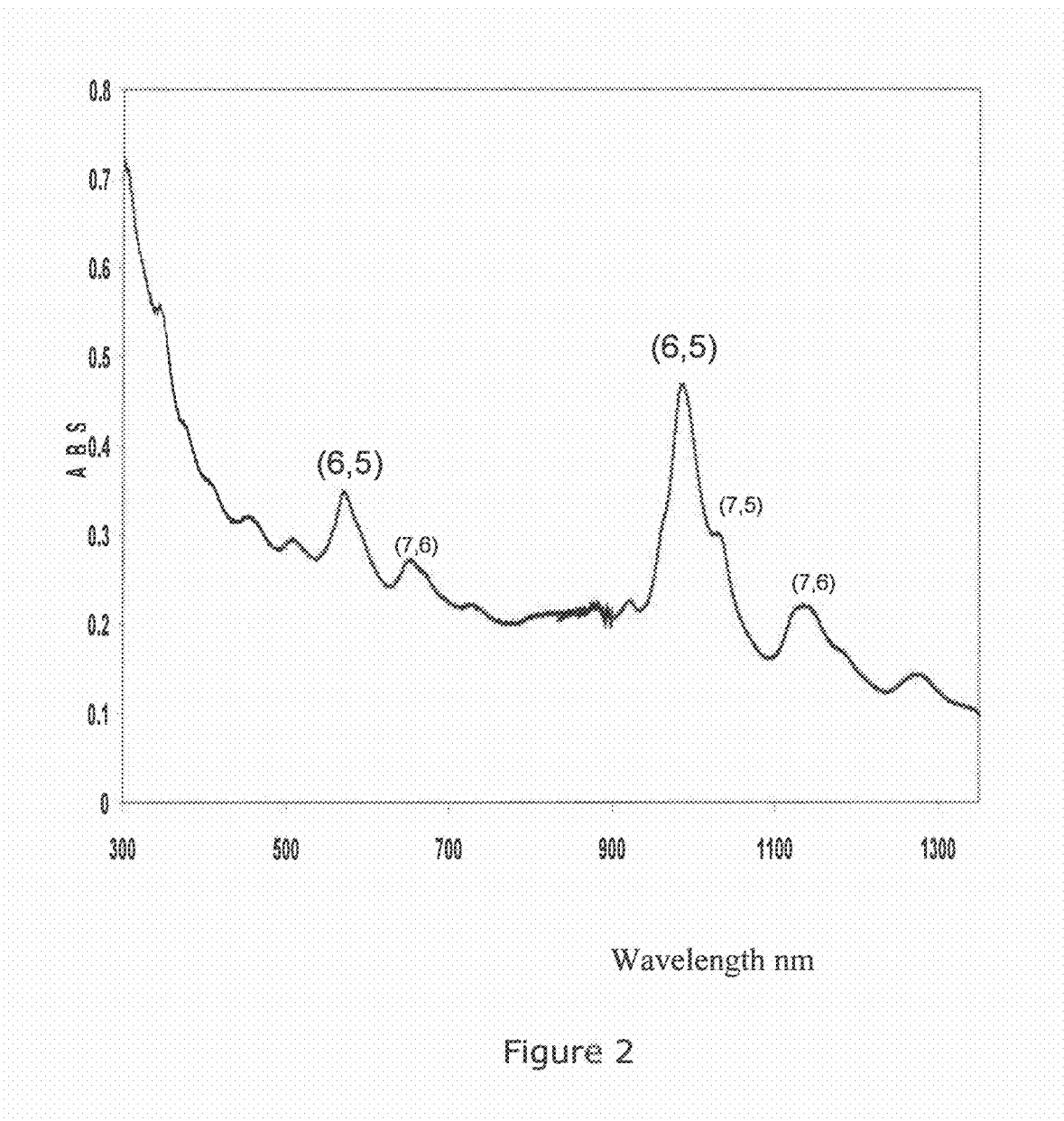
FIG. 2 is a graph showing an optical absorption spectrum of a SWNT composition which demonstrates a peak absorbance at about 980 nm. Parenthetical pairs above major peaks represent (n,m) structures of SWNTs which are absorbing at wavelengths designated on the x-axis.
Figure 3:
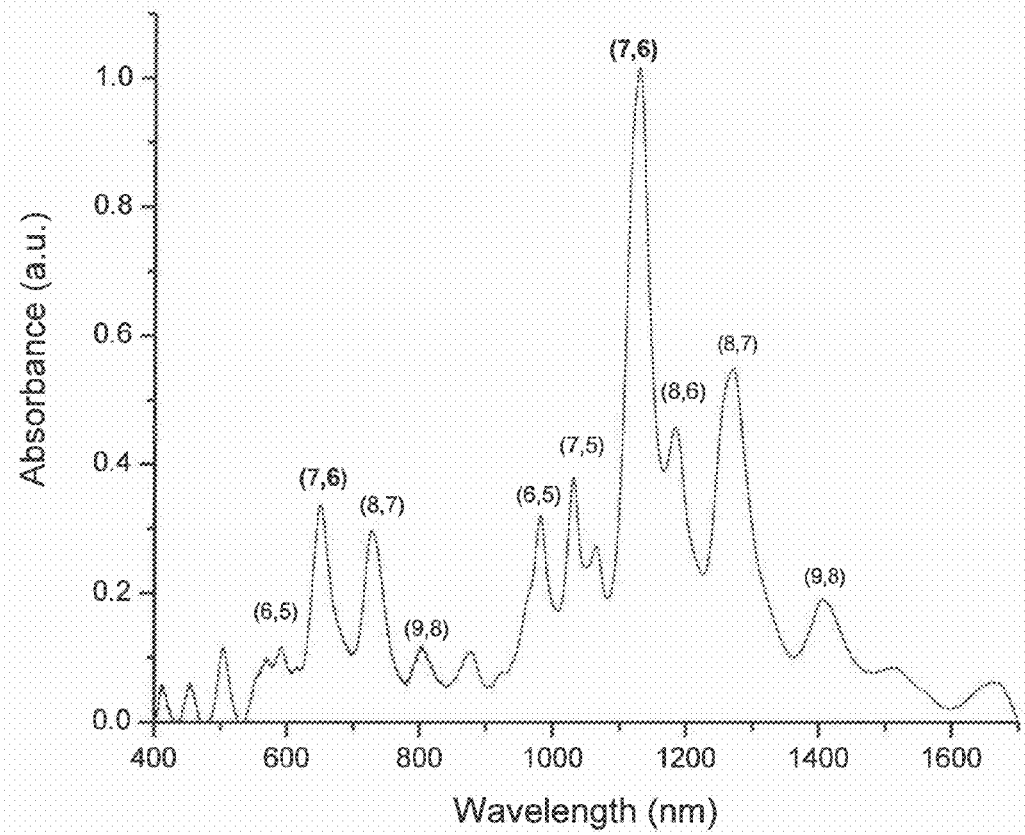
FIG. 3 is a graph showing an optical absorption spectrum of a SWNT composition which demonstrates a peak absorbance at about 1120 nm. Parenthetical pairs above major peaks represent (n,m) structures of SWNTs which are absorbing at wavelengths designated on the x-axis.

As noted above, in some embodiments of the presently disclosed and claimed inventive concept(s), the SWNTs of the protein-SWNT complex are enriched with SWNTs of particular semiconducting (n,m) structures, for example a (6,5), (7,6), or (8,7) structure or combinations thereof (or other contemplated or enabled herein). Thus the therapeutic compositions comprising the protein-SWNT complex comprise a substantial proportion of SWNTs having specific (n,m) structures such as (6,5) and/or (7,6) and/or (8,7) structures. For example, the therapeutic composition may comprise from 10%, from 20%, from 25%, from 30%, from 35%, from 40%, from 45%, from 50%, from 55%, from 60%, from 65%, from 70%, from 75%, from 80%, from 85%, or from 90%, to 95%, or greater of a SWNT having a particular (n,m) structure such as semiconducting (6,5), (7,6), or (8,7) SWNTs or combinations thereof. Also, in one particular embodiment, the intensity of the S11 transition of the SWNTs is at least 50% of the background. Another particular embodiment of SWNTs utilized in accordance with the presently disclosed and claimed inventive concept(s) are SWNTs having a (7,6) structure. SWNTs with (6,5) structure have a strong and narrow absorbance at and near 980 nm (FIG. 2), and SWNTs with (7,6) structure have strong and narrow absorbance at and near 1120 nm (FIG. 3), thus enabling therapeutic use of smaller quantities of these SWNTs and exposure to a more narrowly directed range of wavelengths and lower overall power. SWNTs having (8,7) structure have strong absorbance at and around 265 nm.

The some embodiments described herein the SWNTs used have a non-metallic, semiconducting structure. Examples of such non-metallic, semiconducting SWNTs are shown in Table 4. Nanotubes with metallic structures (i.e., wherein "n−m"=0, or is a multiple of 3) are not suitable for optimal use herein. Semiconducting SWNTs suitable for use herein include, for example, nanotubes wherein "n−m"=1, 2, 4, 5, 7, 8, 10, 11, 13, 14, and 16. For example, for a SWNT with the (n,m) structure (6,5), "n−m"=1.

TABLE 4

| nanotube structure | wavelength in nm | | |
|---|---|---|---|
| (n, m) | Absorbs | Absorbs | Emits |
| (4, 3) | 700 | 398 | 700 |
| (5, 3) | 720 | 522 | 720 |
| (5, 4) | 835 | 483 | 835 |
| (6, 1) | 653 | 632 | 653 |
| (6, 2) | 894 | 418 | 894 |
| (6, 4) | 873 | 578 | 873 |
| (6, 5) | 976 | 566 | 976 |
| (7, 0) | 962 | 395 | 962 |
| (7, 2) | 802 | 626 | 802 |
| (7, 3) | 992 | 505 | 992 |
| (7, 5) | 1,024 | 645 | 1,024 |
| (7, 6) | 1,120 | 648 | 1,120 |
| (8, 0) | 776 | 660 | 776 |
| (8, 1) | 1,041 | 471 | 1,041 |
| (8, 3) | 952 | 665 | 952 |
| (8, 4) | 1,111 | 589 | 1,111 |
| (8, 6) | 1,173 | 718 | 1,173 |
| (8, 7) | 1,265 | 728 | 1,265 |
| (9, 1) | 912 | 691 | 912 |
| (9, 2) | 1,138 | 551 | 1,138 |
| (9, 4) | 1,101 | 722 | 1,101 |
| (9, 5) | 1,241 | 672 | 1,241 |
| (9, 7) | 1,322 | 793 | 1,322 |
| (9, 8) | 1,410 | 809 | 1,410 |
| (10, 0) | 1,156 | 537 | 1,156 |

TABLE 4-continued

| nanotube structure | wavelength in nm | | |
|---|---|---|---|
| (n, m) | Absorbs | Absorbs | Emits |
| (10, 2) | 1,053 | 737 | 1,053 |
| (10, 3) | 1,249 | 632 | 1,249 |
| (10, 5) | 1,249 | 788 | 1,249 |
| (10, 6) | 1,377 | 754 | 1,377 |
| (10, 8) | 1,470 | 869 | 1,470 |
| (10, 9) | 1,556 | 889 | 1,556 |
| (11, 0) | 1,037 | 745 | 1,037 |
| (11, 1) | 1,265 | 610 | 1,265 |
| (11, 3) | 1,197 | 793 | 1,197 |
| (11, 4) | 1,371 | 712 | 1,371 |
| (11, 6) | 1,397 | 858 | 1,397 |
| (11, 7) | 1,516 | 836 | 1,516 |
| (11, 9) | 1,617 | 947 | 1,617 |
| (11, 10) | 1,702 | 969 | 1,702 |
| (12, 1) | 1,170 | 799 | 1,170 |
| (12, 2) | 1,378 | 686 | 1,378 |
| (12, 4) | 1,342 | 855 | 1,342 |
| (12, 5) | 1,499 | 793 | 1,499 |
| (12, 7) | 1,545 | 930 | 1,545 |
| (12, 8) | 1,657 | 917 | 1,657 |

Example 3

Determination of the Dissociation Constant ($K_d$) for the Binding of SWNT-CMC-Annexin V to Human Endothelial Cells In Vitro.

The data obtained above for the binding of SWNT-CMC-annexin V to human endothelial cells in vitro was used in the determination of the dissociation constant ($K_d$). The formation of a ligand-protein complex (C) between a protein (P) and a ligand (L) can be described by the following process at equilibrium:

The dissociation constant is defined as:

$$K_d = \frac{[P][L]}{[C]}$$

where [P], [L], and [C] represent the concentrations of the protein, ligand, and complex, respectively. The smaller the dissociation constant, the more tightly bound the ligand is, or the higher the affinity between the ligand and the protein.

In the calculation of $K_d$, the concentration of SWNT-CMC-annexin V at equilibrium was obtained by subtracting the amount of SWNT-CMC-annexin V bound from the initial amount of SWNT-CMC-annexin V added. The calculation of $K_d$ was performed with Prism 5 software (GraphPad™ Software, La Jolla, Calif.).

Figure 4:
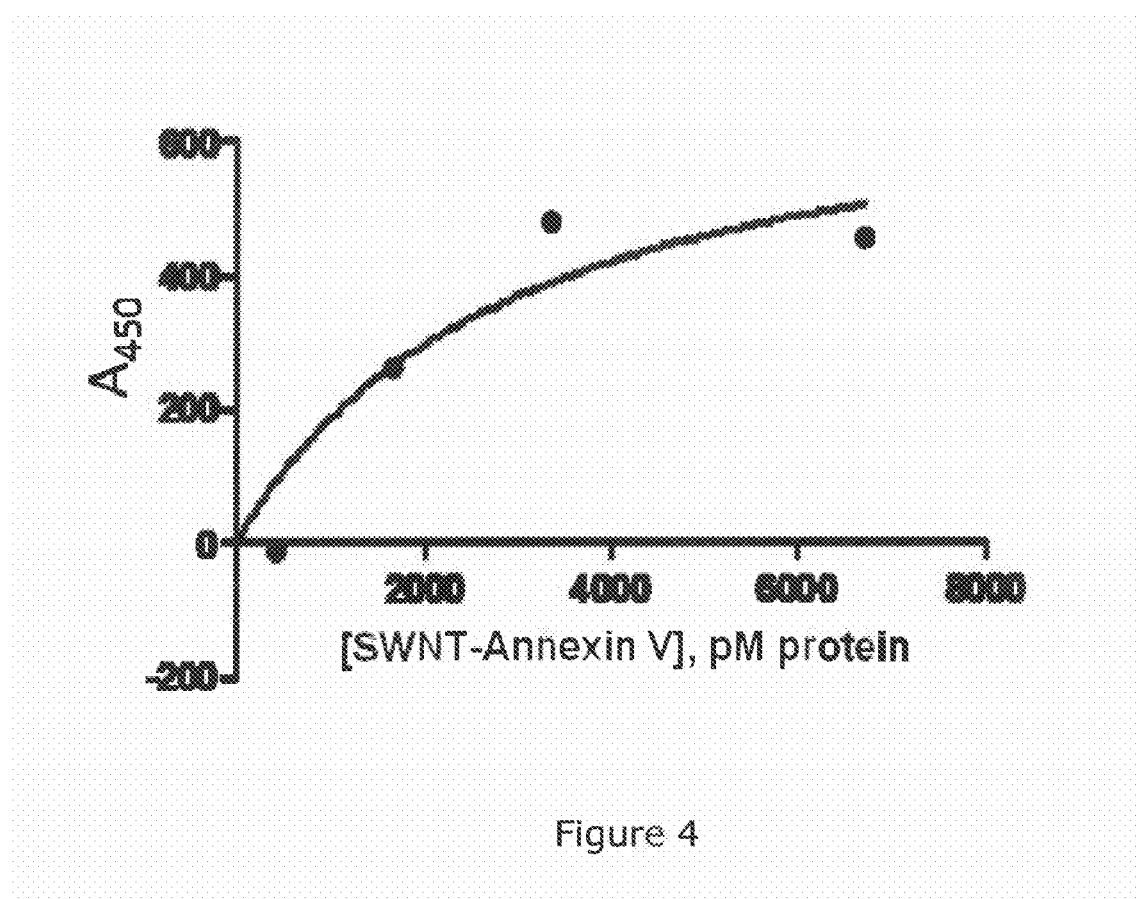
FIG. 4 is a graph showing equilibrium data for the binding of SWNT-annexin to human endothelial cells in vitro. [SWNT-annexin V] is the concentration of the SWNT-annexin V complex at equilibrium. $A_{450}$ is measured after adding the chromogenic substrate O-phenylenediamine (OPD) to endothelial cells with SWNT-annexin V (biotinylated) bound and with streptavidin-HRP bound to the SWNT-annexin V (biotinylated). HRP (horseradish peroxidase) converts to OPD to a colored product with absorbance at 450 nm.

The data used in the calculation of $K_d$ and the fit of the data by the Prism 5™ software is shown in FIG. 4. The $K_d$ obtained from this calculation is 2.9 nM, which indicates a reasonably good affinity of binding.

Example 4

Absorption Spectra for SWNT-CMC-Annexin V and SWNT-CMC.

Figure 5:
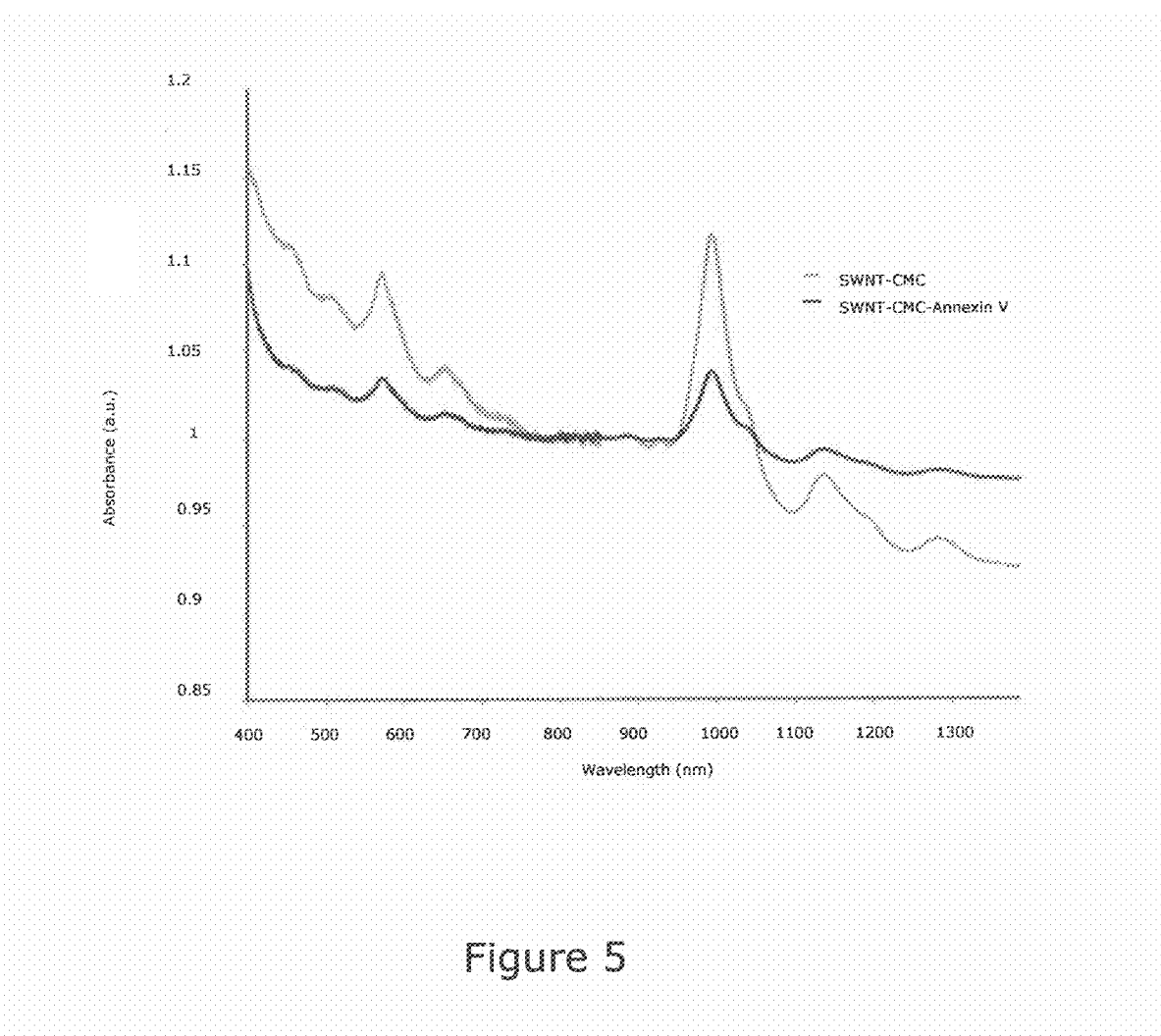
FIG. 5 shows a visible-NIR absorption spectra for SWNT-CMC-annexin V and SWNT-CMC, normalized to 1.00 at 860 nm.

The absorption of light as a function of wavelength was measured using a Bruker Equinox 55 FTIR/FTNIR/FTVis spectrometer; 60 scans at 30 cm$^{-1}$ were averaged on each spectrum in order to achieve a high signal-to-noise ratio. The absorption spectra were normalized to 1.00 at 860 nm. The spectra are shown in FIG. 5. For SWNT-CMC-annexin V, the absorption at 980 nm is reduced compared to SWNT-CMC, but the absorption is still significant (approximately 35% of the absorption for SWNT-CMC).

Example 5

Laser Treatment at 980 Nm of Human Endothelial Cells In Vitro with SWNT-CMC-Annexin V Bound.

The effects of irradiation of SWNTs bound to endothelial cells were tested in vitro. Recombinant annexin V was conjugated to carboxymethylcellulose (CMC) adsorbed to SWNTs using the procedure provided above, except the molecular weight of CMC was 30 kDa. The annexin V in the SWNT-annexin V complex was biotinylated using the procedure given above. The following procedure was used to treat human endothelial cells in vitro with SWNT-CMC-annexin V bound.

Cells were grown using F12K media containing 10% FBS until they reach 85% confluence in T-75 flasks, and the cells were then counted using a hemocytometer. Cancer cells ($5 \times 10^4$) were transferred to 24 well plates (6 plates, with 3 wells per plate containing cells) and grown until 85% confluence was reached. Two extensive dialyses were performed (with a total dilution factor of 1,000,000×) in order to remove the sodium azide from the SWNT-CMC-biotinylated annexin V. The first dialysis for 3 hours (1000×) was performed using modification buffer (100 mM sodium phosphate, 150 mM NaCl, pH 7.2-7.4). The buffer was changed and the dialysis continued for 4 more hours. 1 ml of the suspension of SWNT-CMC-biotinylated annexin V was used. PS was exposed on the surface of cells by the addition of hydrogen peroxide (1 mM), and the cells were treated with 300 µl binding buffer containing the F12K media containing 1 mM of $H_2O_2$ for 1 hour at 37° C. The plates were washed 4× with F12K media (containing 10% FBS) (300 µl), and SWNT-CMC-biotinylated-annexin V (300 µl) was added to wells at a concentration of 20 nM. In order to obtain this concentration, the protein was diluted using F12K media (containing 10% FBS plus 2 mM $Ca^{2+}$). For each plate, the experiment was done in triplets. The plates were incubated for 2 hours in the incubator and then washed 4× with F12K media (containing 10% FBS plus 2 mM $Ca^{2+}$) (300 µl). 300 µl of F12K media with 2 mM $Ca^{2+}$ was added to the wells, and a laser beam was applied at a constant energy density of 20 J/cm² that will cover 4 wells in a square pattern (5.0 cm beam diameter) for 10 and 20 seconds and separate wells for 5 seconds (2.2 cm diameter). For each set of 3 wells containing cells that undergo the same treatment, a different plate (6 plates total) was used in order to minimize the time that the plates are out of the incubator. A LaserCare 50 laser set at 980 nm was used to deliver the laser beam from underneath the plate (Sharplan Medical Systems, Israel). See Table 5. Cell viability was evaluated one hour later by adding Alamar Blue in an amount equal to 10% of culture media (30 µl of Alamar Blue+300 µl of media) volume to the wells. The Alamar Blue was added to the plates at once. The plates were incubated for 4 hours, and the samples (300 µl/well) were transferred to a 96-microtiter plate. Fluorescence was then measured at 590 nm (using excitation at 530 nm). 300 µl of fresh media was added to each well on the 24-well plate immediately transfer to the 96-microtiter plate. The cells that were attached were treated with trypsin, and the cells were combined in the 96-well plates and counted in a hemocytometer.

TABLE 5

| | Time laser on, sec | | Power density, W/cm² | Beam diameter, cm | Power of the beam, W |
|---|---|---|---|---|---|
| Plate 1 (control) | 0 | SWNT + Cells | — | — | 0 |
| Plate 2 (control) | 0 | No SWNT + Cells | — | — | 0 |
| Plate 3 | 5 | SWNT + Cells | P = 4.0 | 2.2 | 15.2 |
| Plate 4 (control) | 10 | No SWNT + Cells | P = 2.0 | 5.0 | 39.27 |
| Plate 5 | 10 | SWNT + Cells | P = 2.0 | 5.0 | 39.27 |
| Plate 6 | 20 | SWNT + Cells | P = 1.0 | 5.0 | 19.64 |

Results of Example 5

Before testing with endothelial cells grown on 24-well plates, tests were performed to determine the laser energy density that would give a minimal temperature rise in the media (300 µl) in the wells. It was found that an energy density of 20 J/cm² (=power density in W/cm²×time in sec) gave a temperature rise of only 1° C. An energy level of 60 J/cm² gave a temperature rise of 4° C., and an energy level of 60 J/cm² gave a temperature rise of 7° C. Therefore, an energy density of 20 J/cm² was used for the tests with endothelial cells, in order that there would not be a deleterious effect on the cells without the carbon nanotubes attached.

Alamar Blue and cell counting are used in order to determine the effect of the laser treatments. Oxidized, blue non-fluorescent Alamar Blue is reduced to a pink fluorescent dye in the medium by the cell activity (47). Alamar is nontoxic to cells and does not necessitate killing the cells in order to obtain measurements.

Figure 6:
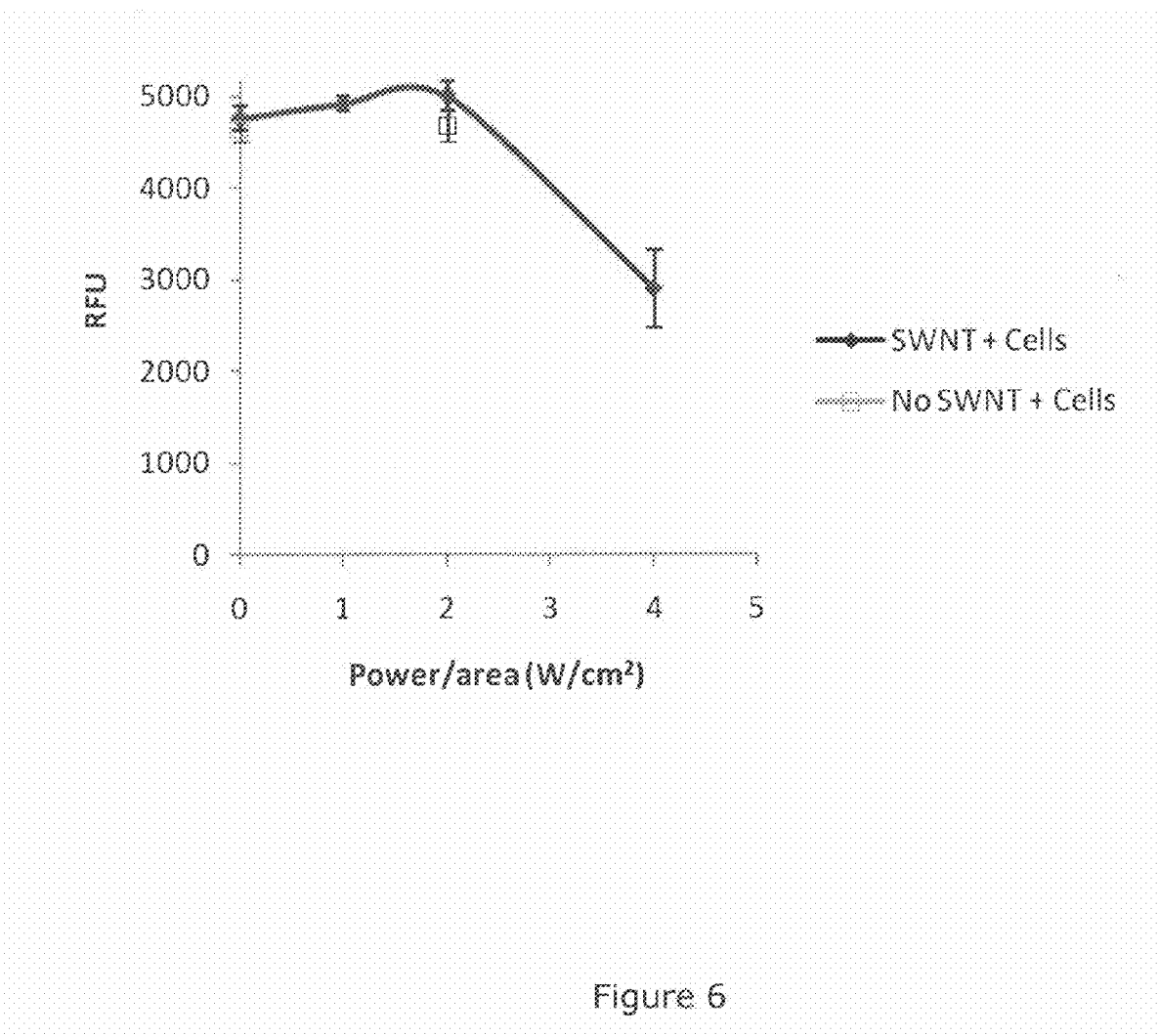
FIG. 6 shows the effect of laser treatment at 980 nm on human endothelial cells in vitro as measured by the Alamar Blue assay. For cells that received laser power, the energy level was 20 $J/cm^2$. RFU is relative fluorescence units. Each data point represents the mean±SEM for three wells.
Figure 7:
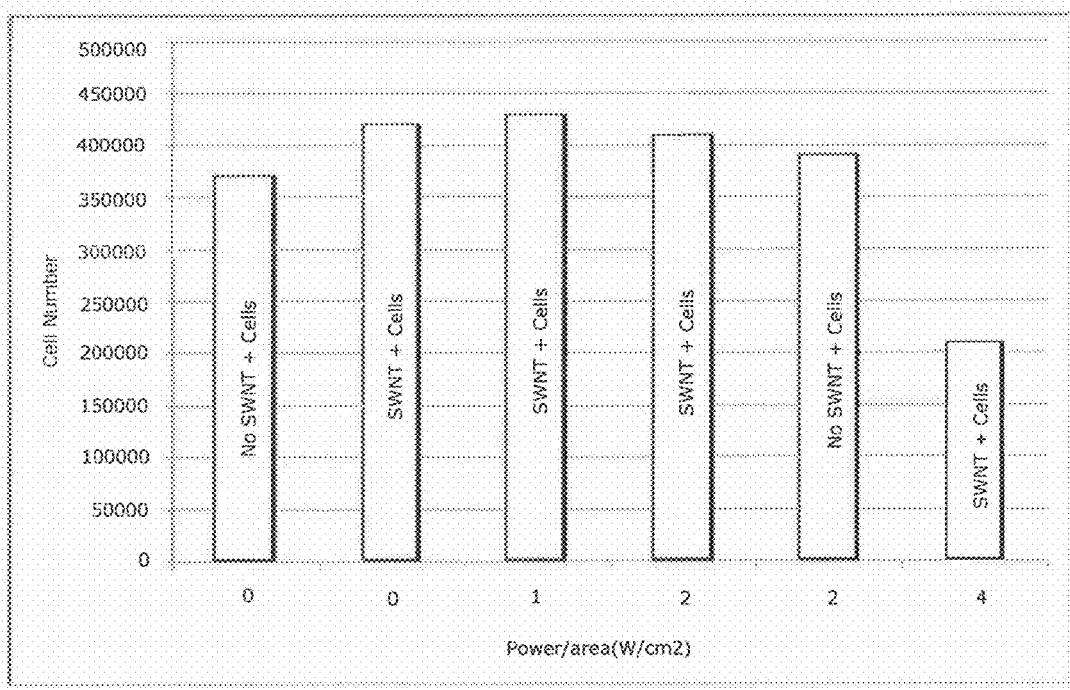
FIG. 7 shows the effect of laser treatment at 980 nm on human endothelial cells in vitro as measured by counting the cells using a hemocytometer. For cells that received laser power, the energy level was 20 $J/cm^2$. Data represent the average number of cells in 10 microscopic fields.

The results are shown in FIGS. 6 and 7. The most notable finding from these results is that the cell viability as measured by Alamar Blue and the cell number were greatly reduced at a power density of 4 W/cm² for cells with SWNT-CMC-annexin V bound compared to power densities of 0, 1, and 2 W/cm² for cells with SNWT-CMC-annexin V bound (for the RFU results, a significance level of p<0.005 using the two-sided T-test). The cell viability and cell number at 4 W/cm² for cells with SWNT-CMC-annexin V were 61% and 50%, respectively, of the cell viability and cell number at 0 W/cm² for cells with SWNT-CMC-annexin V.

At a power level of 2 W/cm², there was no significant difference in the RFU results between cells with nanotubes and cells without nanotubes. With no laser treatment, there was no significant difference in the RFU results between cells with nanotubes and cells without nanotubes. The latter results indicate that the nanotubes do not inherently affect cell viability in the absence of laser treatment.

Power values given in FIGS. 6 and 7 are the power measured at the bottom of the 24-well plate. The laser beam was directed to the plate from underneath the plate. In an separate measurement of power at a power density of 12.7 W/cm² using a plate with no culture media, it was found that there was a 6% loss of power through the plate.

Example 6

Figure 8:
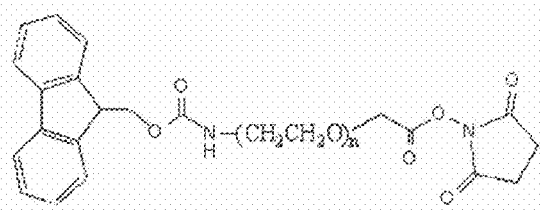
FIG. 8 shows the structure of Fmoc protected amine-PEG-succinimidyl carboxy methyl ester (Fmoc-NH-PEG-NHS (NHS:SCM).

In another embodiment of the presently disclosed and claimed inventive concept(s), an Fmoc protected amine-PEG-succinimidyl carboxy methyl ester (Fmoc-NH-PEG-NHS, see FIG. 8) is adsorbed to SWNTs that are first dispersed using sodium cholate. The SWNT-Fmoc-NH-PEG-NHS is then reacted with the linking protein or peptide (e.g., Annexin) wherein the NHS ester reacts with a reactive amino group in the protein (t-amino of L-lysine or the N-terminal amino group).

Fmoc-NH-PEG-NHS, with the PEG having a molecular weight of 3400 Da, for example, can be used to attach a protein to SWNTs using the following procedure: 3 mg of SWNTs were mixed with 140 mg of sodium cholate (2% w/t) in 7 ml of dionized water. The suspension was sonicated for 30 minutes at a power level of 7 W and then centrifuged for 30 minutes at 29,600×g. The pellet was discarded, and the sonication and centrifugation steps were repeated. The suspension was dialyzed for 12 hours using a 10 kDa dialysis membrane and 2 liters of 20 mM sodium phosphate buffer at pH 7.4. 0.8 mg of Fmoc-NH-PEG-NHS was dissolved in 0.8 ml of deionized water. The Fmoc-NH-PEG-NHS solution was combined with the SWNT suspension and mixed gently for 30 minutes at room temperature. An equimolar amount of the protein was added at a concentration of 1 mg/ml in 40 mM sodium phosphate buffer (pH 7.4) and mixed gently for 30 minutes at room temperature (the protein is equimolar to the Fmoc-NH-PEG-NHS). The suspension was dialyzed at 4° C. for 4 hours and then overnight with 1 liter of sodium phosphate buffer (20 mM at pH 7.4) for each dialysis using a 100 kDa membrane, followed by centrifugation for 1 hour at 29,600×g to remove any aggregated nanotubes.

The procedure described above was applied using the human annexin V protein but any Annexin described herein could be used. After the final centrifugation, the protein concentration was 40 mg/L. The effect of irradiation of human endothelial cells with SWNT-Fmoc-NH-PEG-NHS-annexin V bound was tested in vitro as follows: cells were grown using F12K media containing 10% FBS until they reach 85% confluence in T-75 flasks, and the cells counted using a hemocytometer. Cancer cells ($5 \times 10^4$) were transferred to 24-well plates and grown until 85% confluence was reached. The media was warmed up in the incubator at 37° C. and then removed from the wells. Phosphatidylserine was exposed on the surface of cells by the addition of hydrogen peroxide (1 mM), and the cells were treated with 300 µl binding buffer containing the F12K media and containing 1 mM of H2O2 for 1 hour at 37° C. The plates were washed 1× with F12K media (containing 10% FBS) (300 µl), and SWNT-Fmoc-NH-PEG-NHS-annexin V was added to wells at a concentration of 20 nM protein. In order to obtain this concentration, the protein was diluted using F12K media (containing 10% FBS) plus 2 mM $Ca^{2+}$. For each plate, the experiment was performed in triplets.

The plates were then incubated for 2 hours in the incubator and then washed 4× with F12K media (containing 10% FBS plus 2 mM $Ca^{2+}$) (300 µl). 300 µl of F12K media with 2 mM $Ca^{2+}$ was then added to the wells, and the laser test was performed using a power of 1.50 W/cm$^2$ for 130 seconds (195 J/cm$^2$). Cell viability was evaluated one hour later by adding Alamar Blue in an amount equal to 10% of culture media (30 µl of Alamar Blue+300 µl of media) volume to the wells. The Alamar Blue was added to the plates at once and the plates incubated for 4 hours. The samples (300 µl/well) were then transferred to a 96-microtiter plate, and fluorescence was measured at 590 nm (using excitation at 530 nm).

Figure 9:
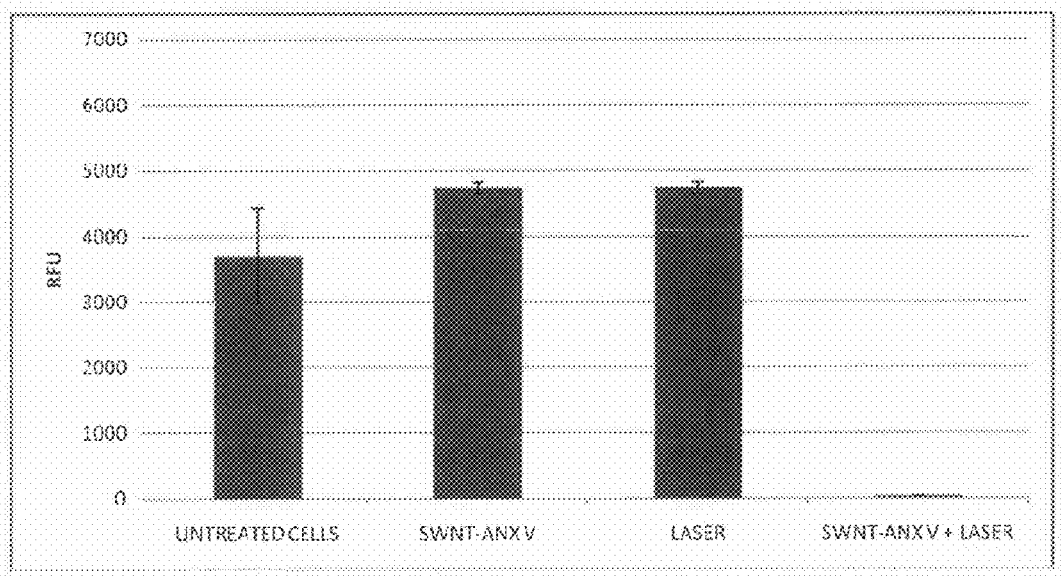
FIG. 9 shows the effect of laser treatment at 980 nm on human endothelial cells in vitro as measured by the Alamar Blue assay. SWNT-ANX V is the SWNT-Fmoc-NH-PEG-NHS-annexin V complex. The laser power was 1.50 $W/cm^2$ for 130 seconds (195 $J/cm^2$). RFU is relative fluorescence units. Each point represents the mean±SEM for three wells. The star (*) indicates that the difference in mean RFU compared to that for the untreated cells is significant using a two-sided t test at a 95% confidence level (p<0.05).

The results are shown in FIG. 9. As can be seen from the results, SWNT-Fmoc-NH-PEG-NHS-annexin V or the laser had no effect on the cells individually, but together they resulted in killing virtually all of the cells.

Example 7

Conjugation of SWNTs to Annexin V-Alternative Method.

In an alternative method, the binding of the linker to the SWNT surface was modified by using the Fmoc-protected amine-PEG-succinimidyl carboxy methyl ester (Fmoc-NH-PEG-NHS) by using sodium dodecylsulfate (SDS) instead of sodium cholate. SDS adsorbs less strongly to SWNTs than sodium cholate (Wenseleers et al. (2004) *Adv Funct Mater,* 14(11):1105-1112). The SWNTs were suspended in an aqueous solution of SDS using sonication. After centrifugation, an aqueous solution of the linker with the same concentration of SDS was added to the SWNT suspension. Dialysis using a 2 kDa membrane was performed to remove SDS (MW=0.28 kDa) but retain the linker (MW=3.78 kDa). The suspension was centrifuged, and an equimolar amount of annexin V (MW=36 kDa) was added. Finally, dialysis was performed with a 100 kDa membrane to remove any unreacted protein, and the suspension was centrifuged. As noted above, any other protein contemplated for use in the presently disclosed and claimed inventive concept(s) may be used in place of Annexin V. The complete procedure was as follows: 3 mg of SWNTs was added to 7 ml of a 1% SDS solution, and the suspension was sonicated for 30 minutes, followed by centrifugation of the suspension for 30 minutes. 5 mg of Fmoc-NH-PEG-SCM was dissolved in 5 ml of the 1% SDS solution, and 8 mg of the protein annexin V was dissolved in 8 ml of 40 mM sodium phosphate buffer (this step must be performed just before the addition of the protein to the suspension in order to avoid protein denaturation). 780 µl of the linker solution was added to the 7 ml of the nanotube suspension and mixed for 30 minutes (1 linker molecule for approximately every 200 benzene rings in the nanotubes). A 24 hour dialysis was performed by using a 2 kDa dialysis membrane, and the buffer (20 mM sodium phosphate buffer at pH 7.4) was changed after 4, 8, and 20 hours from the beginning of the dialysis. The volume of the buffer used was 2 L. The last dialysis step must be performed for 4 hours (volume to be dialysed=7.8 ml). A one hour centrifugation at 29,600×g was performed in order to remove some possible SWNTs aggregates, and 7.4 ml of the protein solution was added to the suspension and allowed to mix with the SWNT suspension for 30 minutes (equal molar ratio to the linker). A 24 hour dialysis was performed by using a 100 kDa dialysis membrane, and the buffer (20 mM sodium phosphate buffer at pH 7.4) was changed after 4, 8, and 20 hours from the beginning of the dialysis. The volume of the buffer used was 4 L. The last dialysis step must be performed for 4 hours (volume to be dialysed=15.2 ml). A one hour centrifugation at 29,600×g was performed in order to remove possible SWNTs aggregates, and the SWNT and protein concentrations were measured after centrifugation.

Figure 10:
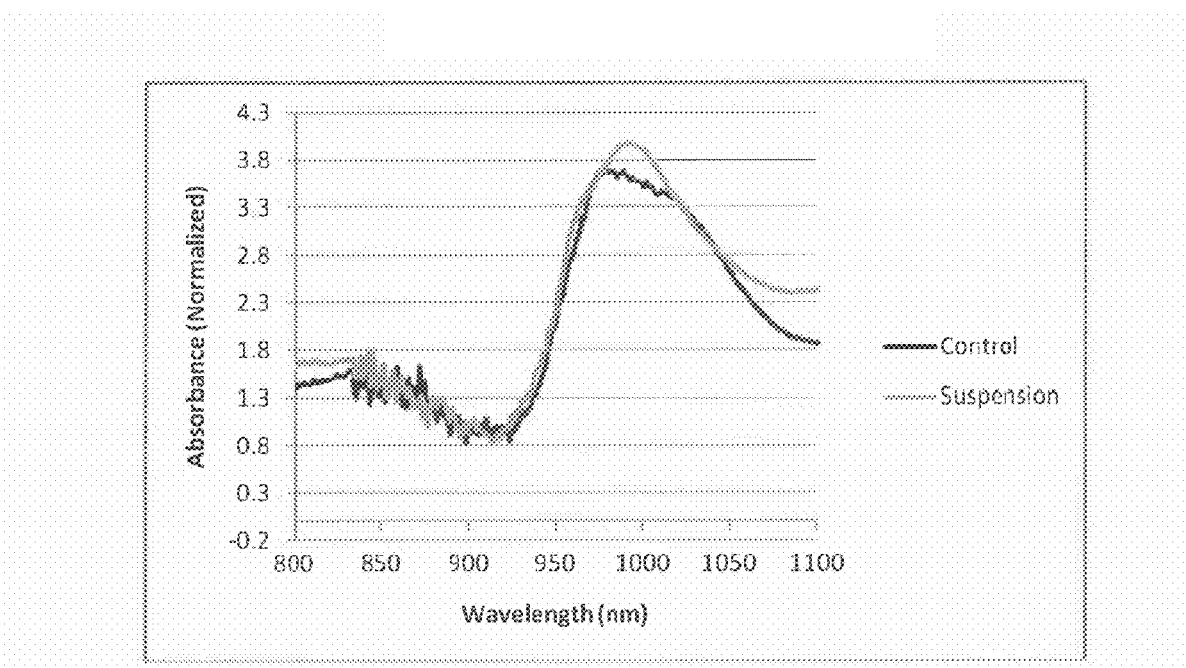
FIG. 10 is a graph showing NIR absorption spectra of SWNTs with annexin V attached via the Fmoc-NH-PEG-NHS linker (suspension) and suspended using SDS (control).

This procedure resulted in an annexin V concentration of 555 mg/liter and a SWNT concentration of 44 mg/liter. The near-infrared (NIR) absorption spectra of the suspension before and after addition of the protein showed that the absorbance peak at 980 nm was completely retained (FIG. 10). There was a slight red shift of ~10 nm in the peak, which the inventors have seen previously when protein was adsorbed on the SWNT surface (Palwai et al. (2007) *Nanotechnology,* 18:235601), and has also been seen by others for adsorbed DNA (Malik et al. (2007) *Composites Science and Technology,* 67(5):916-921). When the SWNTs were suspended by adsorbing the protein horseradish peroxidase, the absorption peak at 980 nm was about 60% of the peak when the SWNTs were suspended using the surfactant sodium cholate (Palwai et al., supra). Thus, it is likely that annexin V is not adsorbing directly to the SWNT surface when the Fmoc-NH-PEG-NHS linker is used in this suspension procedure.

Example 8

Laser Treatment of Human Endothelial Cells with SWNT-Annexin V Complex.

SWNTs with annexin V conjugated using the Fmoc-NH-PEG-NHS linker added via the SDS method were used in a laser test with endothelial cells. The procedure used was as follows: cells were grown using F12K media containing 10% FBS until they reached 85% confluence in T-75 flasks. The endothelial cells were transferred to 24 well plates ($5 \times 10^4$ cells per well) and grown until 100% confluence was reached. A separate plate was used for each different treatment. The media was warmed up in the incubator at 37° C., and the media was removed from the wells. SWNT-annexin V (300 µl) was added to the wells at the concentration desired using F12K media (containing 10% FBS plus 2 mM $Ca^{2+}$) to dilute the suspension. For each plate, the experiment was done with two or three wells.

The plates were incubated for 2 hours in the incubator and then washed 4× with F12K media (containing 10% FBS plus 2 mM $Ca^{2+}$) (300 µl). 300 µl of F12K media was added with 2 mM $Ca^{2+}$ to the wells, and the laser treatment was performed on each well using a beam with a diameter of 1.8 cm, power level of 3.9 W, and beam time of 130 s (energy density=199 $J/cm^2$). Cell viability was evaluated 1 hour later by adding Alamar Blue in an amount equal to 10% of culture media (30 µl of Alamar Blue+300 µl of media) volume to the wells. The Alamar Blue was added to the plates at once.

The samples were incubated for 4 hours; then the samples (300 µl/well) were transferred to a 96-microtiter plate, and fluorescence was measured at 590 nm (using excitation at 530 nm).

Following removal of the media from the wells for two of the treatments, PS was exposed on the surface of cells by the addition of hydrogen peroxide (1 mM). The cells were treated with 300 µl binding buffer containing the F12K media and containing 1 mM of $H_2O_2$ for 1 hour at 37° C. and then washed 1× with F12K media (containing 10% FBS) (300 µl). Then, SWNT-annexing V was added to the wells as described above.

Figure 11:
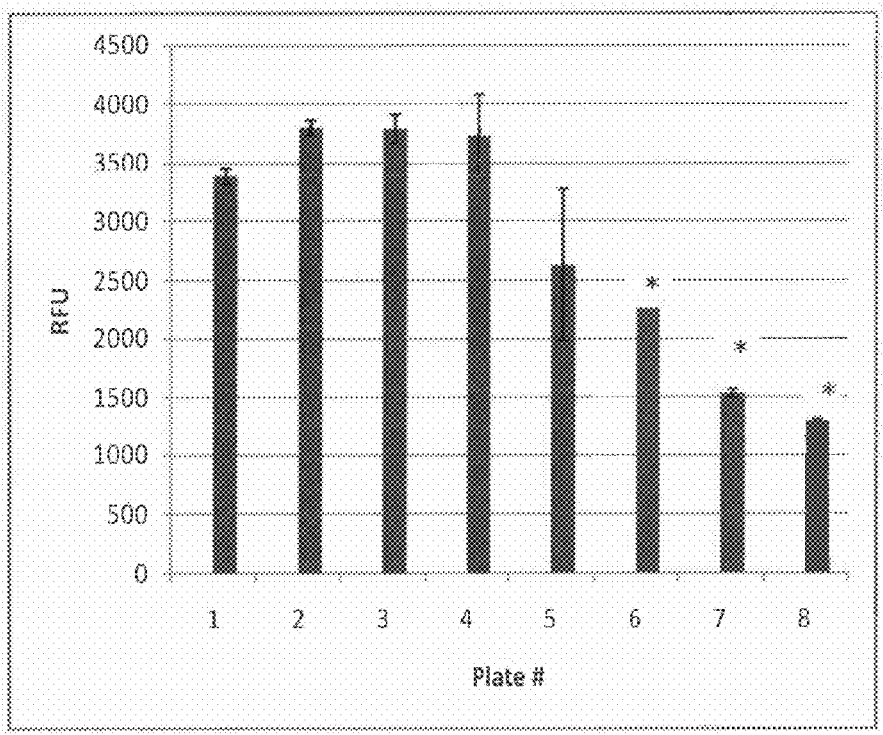
FIG. 11 is a graph showing the effect of laser light at 980 nm on human endothelial cells with SWNT-annexin V bound grown in 24-well plates. RFU is relative fluorescence units. The (*) symbol indicates that RFU is significantly different compared to untreated cells (p<0.05). The bars indicate S.E.

The results of the laser treatment of endothelial cells with SWNT-annexin V bound are shown in FIG. 11 and Table 6. The star symbol (*) above the bars in FIG. 11 indicates that the difference in RFU compared to the untreated cells in plate 1 is statistically significant at $p<0.05$ using the two-sided T-test. The control experiments in plates 1, 2, and 3 indicate that SWNT-annexin V or laser treatment at 199 $J/cm^2$ had no effect on the cells by themselves. The addition of the SWNT-annexin V complex in the presence of the laser at 199 $J/cm^2$ had a concentration-dependent effect on cell viability, which was statistically significant ($p<0.05$) at a SWNT concentration of 0.89 mg/L and laser energy density of 199 $J/cm^2$. With hydrogen peroxide present in the media before the addition of the SWNT-annexin V complex at an energy density of 199 $J/cm^2$, there was a further reduction in cell viability, which was statistically significant compared to the control in plate 1 ($p<0.05$). When the energy density was increased to 299 $J/cm^2$ in the presence of hydrogen peroxide, the cell viability was again lower, which was statistically significant compared to the control in plate 1 ($p<0.05$).

The data in FIG. 11 and Table 6 show that PS was expressed on the cell surface in the absence of hydrogen peroxide, indicating that these cells grown in vitro were under stress, but that the addition of hydrogen peroxide caused more PS to be expressed on the cell surface. Compared to the laser treatment data in Example 6, FIG. 9, which were performed using hydrogen peroxide, less cell killing is observed at the highest SWNT concentration used. This is probably because the experiment shown in Example 8 herein was carried out with cells that were 100% confluent, compared to being 85% confluent in the Example 6 data. Using cells that are 100% confluent is a more realistic simulation of the cell conditions in vivo.

Comparing the results for untreated cells with cells treated with 0.89 mg/L SWNTs, laser energy of 199 $J/cm^2$, and hydrogen peroxide, the cell viability is reduced by 60%. This reduction in cell viability will compromise the vasculature in the tumor and cause the blood flow to the tumor to be cut off.

TABLE 6

| Plate | SWNT, mg/L | Laser energy, $J/cm^2$ | $H_2O_2$, mM |
|---|---|---|---|
| 1 | 0 | 0 | 0 |
| 2 | 0.06 | 0 | 0 |
| 3 | 0 | 199 | 0 |
| 4 | 0.06 | 199 | 0 |
| 5 | 0.15 | 199 | 0 |
| 6 | 0.89 | 199 | 0 |
| 7 | 0.89 | 199 | 1 |
| 8 | 0.89 | 299 | 1 |

In an alternative embodiment of the presently disclosed and claimed inventive concept(s), the protein-CNT complex or protein-SWNT complex and compositions of the presently disclosed and claimed inventive concept(s) can be used with chemotherapeutic agents that have increased effectiveness at temperatures elevated above normal physiologic temperatures. Non-limiting examples of chemotherapeutic agents which can be used herein include mitomycin C, nitrosureas, platin analogs, doxorubicin, mitoxantrone, alkylating agents, bleomycin, and anthracyclins, thiotepa, cis-platin, methotrexate, cyclophosphamide, and amphotericin B. Preferably the chemotherapeutic agents and protein-CNT complexes are administered simultaneously; however, the chemotherapeutic agent may be supplied after the protein-CNT complex has been administered and is ready to be irradiated. The simultaneous treatment with a cytotoxic drug and CNT heating therefore results in the increased killing of cancer cells as compared to when the cytotoxic drug is not administered with the protein-CNT complex. Dosages at which these chemotherapeutic agents are administered in thermo-chemotherapeutic treatments are known by those of ordinary skill, for example as shown in Hahn et al., Zee, and Storm (Hahn et al. (1975) *Proc. Nt. Acad. Sci. USA,* 72(3): 937-940; Zee, J. Van Der (2002) *Annals of Oncology,* 13:1173-1184; and Storm, F. K. (1989) *Radiol. Clin. North Am.,* 27:621-627).

Examples of chemotherapeutic agents which may be administered with the protein-CNT complex or protein-SWNT complex and compositions of the presently disclosed and claimed inventive concept(s) also include immunostimulants which are administered to improve and stimulate the immune system of the subject, as further described herein below.

The protein-carbon nanotube complexes and compositions of the presently disclosed and claimed inventive concept(s) can be administered by intravenous or intratumoral injection, for example, or by any other appropriate method known by those of ordinary skill in the art. A therapeutically effective amount of the composition of the presently disclosed and claimed inventive concept(s) is that amount sufficient to reduce or inhibit growth in or decrease the size of a cancer or tumor in a subject. The therapeutically effective amount administered to the patient will be determined on an individual basis and will be based, at least in part, on consideration of the individual's size, the severity of cancer or tumor to be treated, and the results sought.

In preparing the dosage of protein-carbon nanotube complex to be administered, a variety of pharmaceutically acceptable carriers can be utilized. The carrier, diluent or vehicle may contain a buffering agent to obtain a physiologically acceptable pH, such as phosphate-buffered saline, and/or other substances which are physiologically acceptable and/or are safe for use. In general, the material for intravenous injection in humans should conform to regulations established by the Food and Drug Administration, which are available to those in the field. Pharmaceutically-acceptable carriers may be combined, for example, in a 1 volume: 1 volume ratio, with the protein-carbon nanotube complex or composition. The carrier may be for example, M199 or RPMI 1640 medium. Furthermore, in preparing said dosage form, various infusions in common use today can also be employed.

In an alternate embodiment of the photodynamic therapy of the presently disclosed and claimed inventive concept(s), the protein-CNT complex is combined with or used with an immunostimulant (before, concurrently or after administration of the protein/carbon nanotube complex). Without wishing to be bound by theory, it is thought that the destruction of the endothelial cells in the tumor vasculature and of the tumor's cancer cells causes tumor antigens to be released into the bloodstream. Tumor antigens alone are often not sufficient to stimulate an appropriate immune response. However, the addition of an immunostimulant has been shown to significantly enhance the immune response of the host to the tumor cells, which allows the immune system to mount a systemic attack on the remaining cells of the tumor treated by photodynamic therapy and on the untreated metastases. In non-limiting examples, dosages of immunostimulants may be in the range of 0.001 to 1000 mg per kg of body weight per day, for example depending on the method of administration. Among the immunostimulants which may be used herein include but are not limited to glycated chitosan, muramyldipeptide derivatives, QS21, 3D-MPL or MPL, Quil A, MTP-PE, Poly I:C, AS-101, trehalose-dimycolates, BCG-cell wall skeleton, various cytokines such as IL-2, and INF-α, cyclophosphamide, and monophosphoryl Lipid A.

Other immunostimulants which may be used in embodiments of the presently disclosed and claimed inventive concept(s) include, but are not limited to, those described in WO 96/02555 and in U.S. Pat. Nos. 7,323,182; 7,232,181; 7,316,813; 7,205,284; 7,070,778; 7,038,029; 7,033,591; 6,767,890; 6,752,995; 6,716,430; 6,635,261; 6,610,308; 6,565,856; 6,410,515; 6,153,601; 6,139,844; 6,096,307; 5,890,913; 5,814,611; 5,759,992; 5,747,475; 5,744,452; 5,688,771; 5,420,347; 5,262,425; 5,246,951; 5,240,914; 5,158,941; 5,084,386; 5,079,231; 5,077,284; 5,073,630; 5,041,535; 5,019,568; 4,987,237; 4,937,327; 4,916,119; 4,851,388; 4,801,578; 4,767,743; 4,737,521; 4,716,151; 4,661,512; 4,597,967; 4,581,372; 4,578,399; 4,501,693; 4,407,825; 4,399,124; 4,376,124; 4,226,869; 4,191,778; 4,153,684; 4,148,889; 4,148,885; and 4,001,395, the entireties of each of which are hereby expressly incorporated herein.

As noted, the methods described herein above may further include the step of administering an effective amount of the immunostimulant, wherein the immunostimulant is effective in significantly enhancing the immune response of the patient against the tumor cells, and thereby allowing the immune system to mount a systemic attack on the remaining cells of the tumor. Thus, the presently disclosed and claimed inventive concept(s) are also directed to compositions comprising the protein-carbon nanotube complexes described herein in combination with immunostimulants such as, but not limited to, those described herein and in the publications described hereinabove. The immunostimulant may be administered at the same time as the protein-carbon nanotube complex, or may be administered before or after the administration of the protein-carbon nanotube complex. Or the immunostimulant may be administered after the protein-carbon nanotube complex is administered, but before the irradiation step (or after the irradiation step). Alternatively, the immunostimulant may be administered multiple times to the patient. Dosages of immunostimulants may be in the range of 0.001 to 1000 mg per kg of body weight per day for example depending on the method of administration.

Example 9

In vivo Study: Laser Treatment of Implanted 4T1 Mammary Tumors in Mice with SWNT-Annexin V Complex.

In another embodiment, female BALB/cJ mice, age 6 weeks (received from Jackson Laboratory (Bar Harbor, Me.) were treated. Animal experimentation was not started until the animals were 9 weeks old. The animals were kept in a dedicated room in the animal facility located in the Zoology building of the University of Oklahoma. All of the protocols used involving animals were previously submitted and approved by the Institutional Animal Care and Use Committee (IACUC). All of the animals were placed in appropriate cages with food and water in an adequate environment. Each cage hosted five animals. The anesthetics used were ketamine (100 mg/ml) and xylazine (20 mg/ml). In order to prepare the anesthetic solution, 1 ml of ketamine (100 mg/ml) was mixed with 0.5 ml of xylazine (20 mg/ml) and 8.5 ml of sterile saline solution (0.9% NaCl). The dosage used for each animal was equal to 0.1 ml of the stock solution per 10 grams of body weight. Prior to anesthetizing the animals, each of them was weighted using a scale.

In order to evaluate the ability to eradicate the tumors using this therapy in vivo, it was necessary to implant a suitable cancer cell line in the animals. The 4T1 cell line was chosen for this study, since these cells have the ability to replicate at a fast rate and also develop visible tumors in BALB/c mice in a matter of less than one week after implantation. The methods used to grow these cells in vitro are described on the Cell Culturing and Cell Counting section in U.S. Provisional Ser. No. 61/734,802. After having the eight T-75 flasks growing for 2 days, there are plenty of cells to inject the animals, for each test. The cells are then lifted from the flasks using ACCUTASE® solution (Innovative Cell Technologies, San Diego, Calif.), using the same procedure as for human endothelial cells. The cells are then resuspended in 80 ml of cell medium prior to cell counting. Knowing that it is necessary to inject $5 \times 10^5$ cells/animal (volume=100 μl), the total number of cells was determined. The cell concentration in the sample was evaluated using the standard cell counting procedure. The required cells per animal were then placed in Eppendorf vials and immersed in a chilled water bath. Matrigel was also placed in Eppendorf vials (volume=100 μl), and transferred to the water bath.

This water bath had the function of keeping the cells and the matrigel cold during the transportation of the materials to the animal facility.

As a basis of our theory, the laser irradiation would be responsible for heating within the tumor. In order to check this hypothesis in vivo, the animals were injected i.v. with suitable nanotube suspensions conjugated with the protein annexin V. Before performing those tests, the irradiation safety level had to be determined for the mice. The highest energy level tolerated by the animals without compromising their normal functions was evaluated. For these tests three different energy levels were used: 200 J/cm$^2$, 300 J/cm$^2$, and 400 J/cm$^2$. Prior to the laser irradiation, the three mice used were shaved on the flank using a multipurpose electric razor. The fur was removed in order to eliminate any attenuation of laser energy due to blocking and to help maximize the amount of energy delivered on the region of interest. The area of the irradiating beam was equal to 1.77 cm$^2$ for the majority of the animals. When necessary, the beam size was adjusted to a larger size in order to make sure that the entire tumoral region was being irradiated. The three animals were anesthetized prior to the irradiation session. The power used was 1 W/cm$^2$.

Intratumoral injections of the SWNT-annexin V conjugated were also performed in order to evaluate the efficiency of the treatment when comparing with the i.v. injections. Four mice were used for this study.

For the main photodynamic therapy study, 36 animals were used. The animals were separated into six different groups: Untreated, SWNTs, Laser, SWNTs+Laser, CY and CY+SWNTs+Laser (CY: cyclophosphamide). The first three groups and the CY group were control groups that were used as comparison with the treatment groups (SWNTs+Laser and CY+SWNTs+Laser). When the average tumors volume was approximately equal to 60 mm$^3$, the therapy was started. At that point, the CY and CY+SWNTs+Laser groups received the pro-drug cyclophosphamide i.p. at a dosage of 50 mg/kg. Twenty four hours post-administration, the animals from the SWNTs, SWNTs+Laser and CY+SWNTs+Laser received an i.v. administration of the SWNT-annexin V conjugates. The laser irradiation of the animals from the Laser, SWNTs+Laser, and CY+SWNTs+Laser groups was conducted 24 hours later.

After irradiation, the tumor volumes were monitored every two days. This was done in order to verify the efficiency of the treatment and compare the sizes among the different groups. Prior to the measurements, the animals were sedated and then they were also weighted using a scale. The length and width of the tumors was measured using a digital caliper. The tumor volumes were determined by applying the following formula:

$$T_{volume} = \frac{(length \times width)^2}{2}$$

Figure 12:
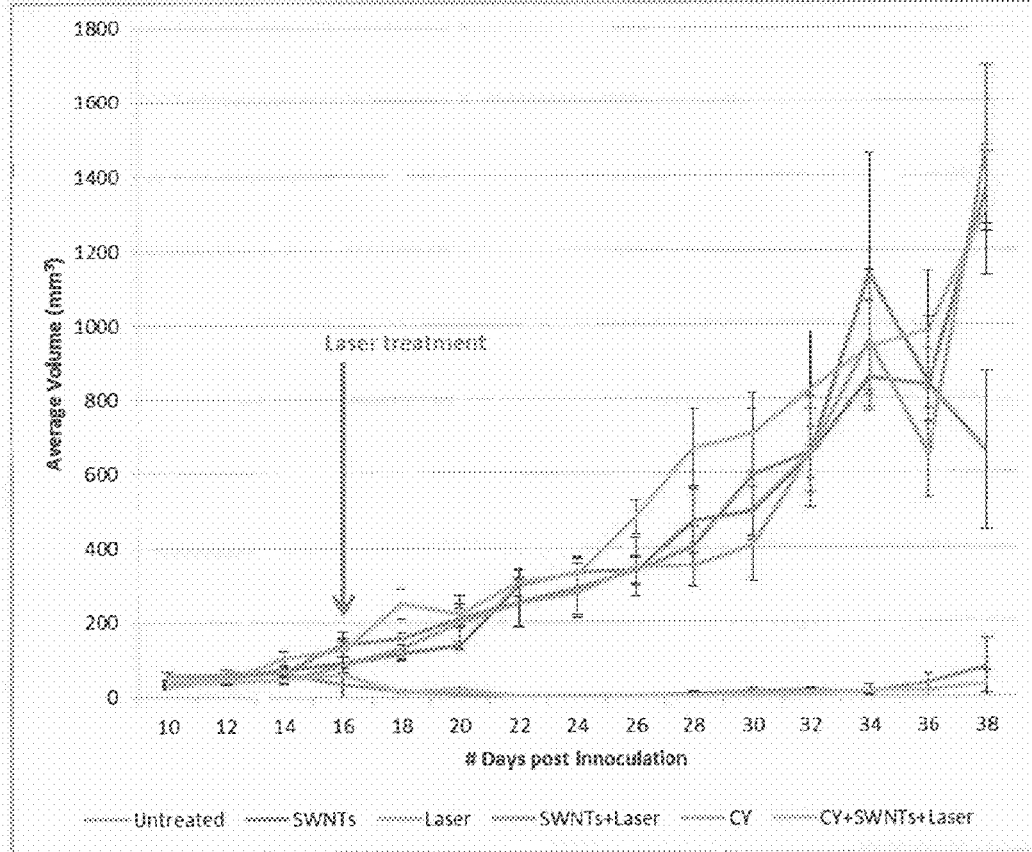
FIG. 12 is a graph showing results of treatment of BALB/cJ mice with implanted 4T1 mouse mammary tumors in Example 9. The doses injected i.p. were 50 mg/kg cyclophosphamide (CY) and 0.82 mg SWNT/kg (109.1 SWNT mg/L, 150 µL). The laser energy and power density were 175 J/cm$^2$ and 1 W/cm$^2$ (time=175 s). Data are presented as the mean±SE (n=6), and statistical significance compared to untreated cells is denoted by * (p<0.01).
Figure 14:
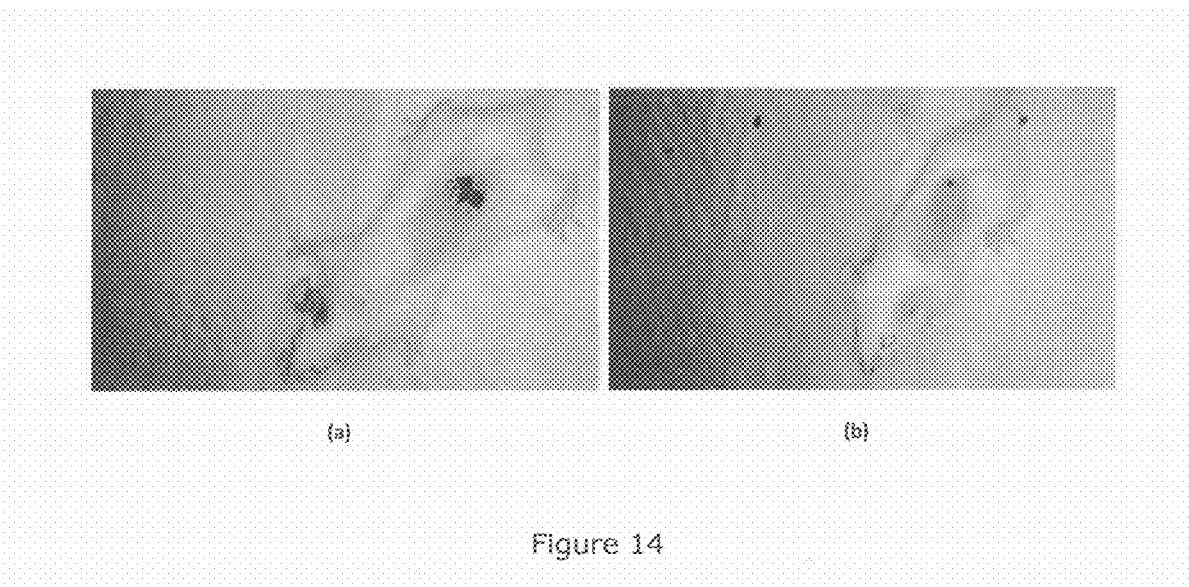
FIG. 14 shows pictures of two mice from the in vivo study of Example 9. (a) Animal treated with the SWNT-annexin V conjugate and NIR irradiation. The tumor completely regressed after therapy. (b) Animal from the untreated group where there was no tumor regression.

The in vivo test results for BALB/cJ mice with 4T1 mouse mammary tumor implants are shown in FIG. 12. Using a tagging system, changes in each animal could be monitored. The tumor sizes in the two groups treated with the laser (SWNTs+Laser and CY+SWNTs+Laser) were significantly lower than those in the untreated group from 16 days after cell inoculation (p<0.01). After the laser treatment, the tumors in the two groups treated with SWNTs steadily reduced in size, and 11 days later (at day 26), there were no animals with visible tumors in the SWNTs+Laser and SWNTs+Laser+CY groups. A few days later, the reoccurrence of palpable tumors was detected in three animals (two from the SWNTs+Laser and one from the SWNTs+Laser+CY groups). These tumors were growing outside of the area treated with the laser, so it is believed that they did not receive a full treatment. It was decided to re-treat these three animals at day 37, by repeating the same protocol previously used on days 13 through 15. Before that day, one of the animals in the SWNTs+laser group died, possibly due to the high degree of metastasis. During the irradiation conducted on day 37, the other animal from the SWNTs+laser group also died. It is suspected that the animal was too weak to resist the irradiation session. The only animal that was treated ended up dying on day 46 with an average tumor volume of 415 mm$^3$. It is possible to postulate that the tumor volume was too high (Volume=212 mm$^3$, which was approximately 2× larger than the volume that was originally irradiated) when the animal was subjected to the laser irradiation, leading to the non-survival of the animal much longer. FIG. 14 illustrates the difference in appearance between an animal from the untreated group and another animal from one of treatment groups.

Figure 13:
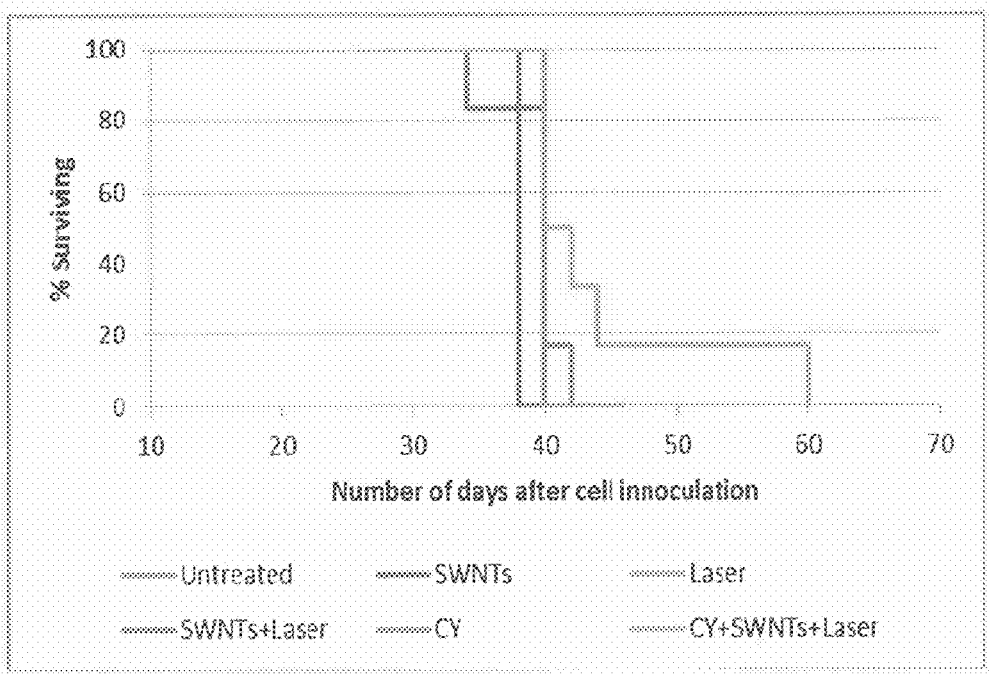
FIG. 13 is a graph showing a survival curve for the in vivo study of Example 9. Euthanasia was performed on any animal that showed signs of discomfort. The first animal that died was from the untreated group and that death occurred on day 34. On day 39 and while performing the second irradiation session, one of the animals present in the SWNTs+Laser group did not survive. On this day, the remaining animals from the Untreated group and one animal from the Laser group were sacrificed. By day 42 all of the animals from SWNTs+Laser were dead. There was one animal in the CY+SWNTs+Laser group that had a significantly longer longevity, being alive until day 59, which corresponds to a survival of 44 days post-irradiation.

The in vivo study was conducted for 60 days since the inoculation of the cancer cells into the animals. The majority of the animals stayed alive until day 38, as shown in the survival curve (FIG. 13). Some of the animals died naturally, while some of them were euthanized based on the presence of signs of possible discomfort. The animals from the CY+SWNTs+Laser had the better survival rate from the study. One animal had a significantly longer longevity being alive until day 59, which corresponds to a survival of 44 days post-irradiation.

After euthanizing the animals, a total of six animals were chosen for further evaluation, two from each of the untreated group, SWNTs+laser group, SWNTs+laser+CY group. For the latter two groups, mice with no visible tumors were chosen. The tumors, lungs, and livers were dissected out and preserved in 10% formalin. The number of metastatic nodules was counted in the lungs, and the results are shown in Table 7. The number of these nodules in the lungs was negligible for 2 animals from the SWNTs+Laser group and for one animal from the CY+SWNTs+Laser group. One of the animals from the CY+SWNTs+Laser group that was dissected exhibited a relatively small number of visible nodules. It is therefore likely that there were already metastases to the lungs for some animals when the laser treatment was carried out at 15 days from the injection of tumor cells. The injection of CY in conjunction with laser+SWNT treatment, intended to boost the immune response to the tumor, did not lead to fewer metastatic nodules compared to laser+SWNT treatment alone.

Figure 15:
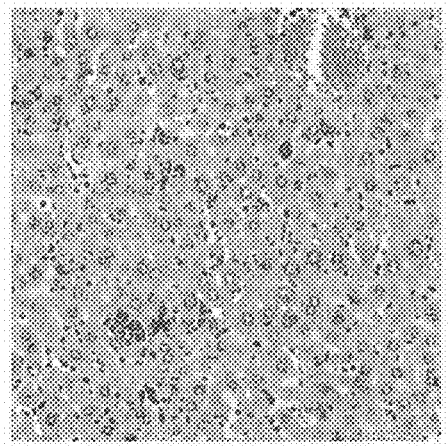
FIG. 15 shows histological images for different specimens collected from one of the animals from the untreated group (a-d) and treated group (e-f) in Example 9. (a) Sectional image of a portion of the liver (40×) with evidence of metastases present on the left side of the black asterisk. (b) Sectional image of the liver (40×) with multiple perivascular focal aggregates consisting mostly of neutrophils evidenced on the left side of the black asterisks. (c) Sectional image of the tumor (40×) illustrating a large necrotic mass denoted by the black asterisk. The region that surrounds the black+ symbol presents a large number of atypical cells that were viable. (d) Sectional image of a portion of the lung (40×) with evidence of metastases in the blood vessel (denoted by the black asterisk) and also in the periphery. (e) Sectional image of a portion of the skin (10×), collected from the original tumor site, showing an intact epithelial layer without the presence of any atypical cells. (f) Sectional image of a portion of the lung (20×) displaying a normal morphology with very distinct alveolar sacs.
Figure 15:
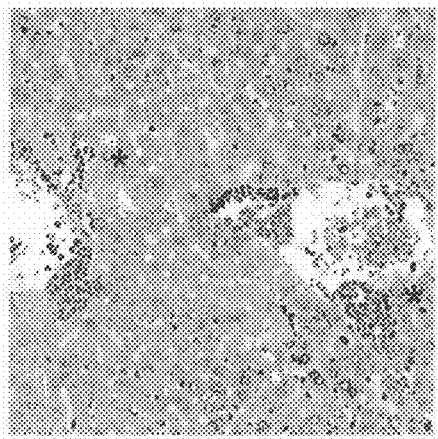
Figure 15:
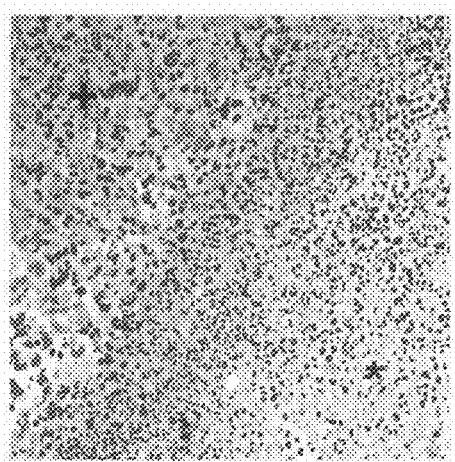
Figure 15:
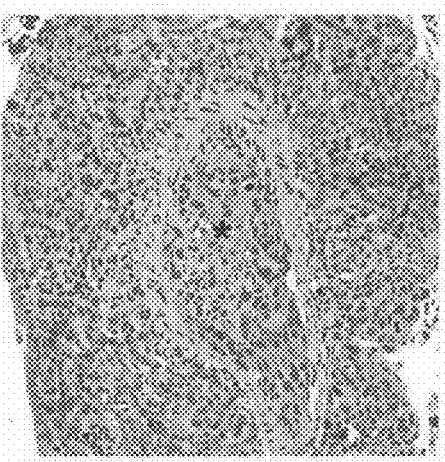
Figure 15:
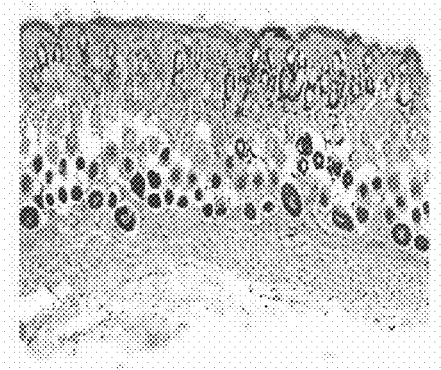
Figure 15:
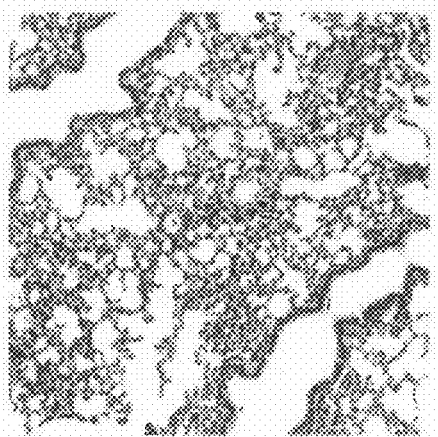

The majority of the animals from the treatment groups (SWNTs+Laser and CY+SWNTs+Laser) completely regenerated the epithelial layer on the irradiation site, with absence of the black scar and fur regrowth. This visual observation correlated with the histological analysis as shown in the Table 8. The specimens were sent for histological analysis at the University of Oklahoma Health Sciences Center (Oklahoma City, Okla.). The qualitative analysis is shown on FIG. 15 and Table 8. The animals from the untreated group presented multiple micro- and macrometastases in the lungs and liver. There was also the evidence of neutrophils in the liver, which is suggestive of a leukomoid response and may be strain-related. The normal tissue in the lungs was almost absent. The tumor masses presented extensive ischemic necrotic areas, with the presence of an abnormal epithelial cell layer.

TABLE 7

METASTATIC NODULE EVALUATION

| Animal # | Group | Number of Visible Nodules |
|---|---|---|
| 1 | Untreated | 16 |
| 4 | Untreated | 18 |
| 19 | SWNTs + Laser | 0 |
| 21 | SWNTs + Laser | 0 |
| 31 | Cy + SWNTs + Laser | 0 |
| 32 | Cy + SWNTs + Laser | 4 |

On other side, three animals of the treatment group were completely free of metastases, presenting intact morphology in the lungs and liver. The samples collected from the tumoral sites evidenced an epithelial layer with an intact and preserved morphology, without evidence of tumoral cells. However, one of the animals from the CY+SWNTs+Laser had metastases present in the lungs and liver. This result shows the variability among the organisms, which can possibly be explained by having metastases forming prior to the treatment start. The original tumoral site had the same appearance as the other animals from the treatment group, i.e., absence of any evidence of tumor cells.

As seen from the histological analyses, there were metastases present in the lungs for some of the animals which is the most suggested cause of death. From a literature analysis, 4T1 cells are known for being poorly immunogenic and highly metastatic inducing metastases even before the tumors are palpable for this particular animal strain. It has been also reported that even if there is complete tumor eradication the most common cause of death is lung failure because of tumor metastases.

These results demonstrated either tumor regression or eradication in the animals in the treatment groups. One day after the laser irradiation of the animals, there was already a significant difference in the average tumor volumes between the animals from the treatment group and the untreated animals. At one point after laser treatment in the two treatment groups, there were no animals with visible tumors; later in a few animals there was tumor regrowth outside the area of the laser beam. There was black scar formation specifically on the area where the tumor was; however there was no visible scar on the surrounding area, which was also subjected to irradiation. Another finding is that the skin epithelial layer in the area of the tumor was completely regenerated, with the absence of the black scar and tumor regrowth for the majority of the animals in the group treated with SWNTs and the laser. A biodistribution study (see U.S. Provisional Ser. No. 61/734,802) revealed that there was a SWNT accumulation in the tumor, liver, and kidney 24 hours post administration. Compared to a study by another group that used non-targeted SWNTs and laser treatment of the same tumors in mice (Robinson et al. Nano Research, 2010, 3(11): pp. 779-793), tumor eradication was achieved in this study using a much lower dosage of SWNTs (approximately four times lower) while resulting in a similar concentration of SWNTs in the tumor.

TABLE 8

Histological Analysis Obtained For Specimens Collected From Six Animals

| Animal # | Group | Lungs | Liver | Tumor |
|---|---|---|---|---|
| 1 | Untreated | Multiple macroscopic metastases present on the surface; evidence of invasion of the chest tissue. Almost complete absence of normal tissue. | Multiple perivascular locations contained a focal aggregate consisting mostly of neutrophils. This is suggestive of a leukomoid response and may be strain-related. Numerous microscopic metastases found in the sinusoids. Almost complete absence of normal tissue. | Extensive ischemic necrosis in the mass. It was comprised of mostly atypical-appearing cells ranging from oval to spindle-shaped |
| 4 | Untreated | High degree of macroscopic metastases, with extensive metastatic foci. Almost complete absence of normal tissue. | Multiple perivascular locations contained a focal aggregate consisting mostly of neutrophils. This is suggestive of a leukomoid response and may be strain-related. The area occupied by the micrometastases was lower than the animal #1 and not so severe. Almost complete absence of normal tissue. | About 66% of the mass appeared to be necrotic, probably as result of ischemia. Epithelial cell layer was not viable. |
| 19 | SWNTs + Laser | Intact morphology and free of metastases. | Intact morphology and free of metastases. | No evidence of the original tumor. Epithelial layer presents an intact morphology. |
| 21 | SWNTs + Laser | Intact morphology and free of metastases. | Intact morphology and free of metastases. | No evidence of the original tumor. Epithelial layer presents an intact morphology. |
| 31 | CY + SWNTs + Laser | Intact morphology and free of metastases. | Intact morphology and free of metastases. | No evidence of the original tumor. Epithelial layer presents an intact morphology. |
| 32 | CY + SWNTs + Laser | Presence of some metastases. | The incidence of intrasinusoidal atypical cells, suggestive of micrometastasis was lower than the animals from the Untreated group. | No evidence of the original tumor. Epithelial layer presents an intact morphology. |

Notably, the epithelial cell layer was intact as observed by the histology analysis in the epithelial area where previously there were tumors in the mice examined in both treatment groups. In addition, the dark scars where the tumors were treated in both treatment groups had returned to a normal skin color by the end of the study for the majority of the animals.

The addition of CY did not translate into a significant difference in terms of tumor volume reduction; however, there was an increased survival of animals in the treatment group that received CY compared to the treatment group that did not.

While the presently disclosed and claimed inventive concept(s) have been described in connection with certain embodiments in the examples herein so that aspects thereof may be more fully understood and appreciated, it is not intended to limit the claims presented below to these particular embodiments. On the contrary, it is intended to cover all alternatives, modifications and equivalents as may be included within the scope of the presently disclosed and claimed inventive concept(s) as defined herein. Thus, these examples include specific embodiments which serve to illustrate the practice of the presently disclosed and claimed inventive concept(s), however, it will be understood that the particulars shown are by way of example and for purposes of illustrative discussion of specific embodiments of the presently disclosed and claimed inventive concept(s) only and are presented in the cause of providing particularly useful and readily understood description of formulation procedures as well as of the principles and conceptual aspects of the presently disclosed and claimed inventive concept(s). For example, although the presently disclosed and claimed inventive concept(s) have been described in detail, it should be understood that various changes, substitutions and alterations can be made herein without departing from the spirit and scope of the presently disclosed and claimed inventive concept(s), particularly as defined by the appended claims. Moreover, the scope of the present disclosure is not intended to be limited to the particular embodiments of the process and compositions, methods and steps described in the specification. As one of ordinary skill in the art will readily appreciate from the present disclosure, processes, compositions, methods, or steps, presently existing or later to be developed that perform substantially the same function or achieve substantially the same result as the corresponding embodiments described herein may be utilized according to the presently disclosed and claimed inventive concept(s). Accordingly, the appended claims are intended to include within their scope such processes, compositions, methods, or steps.

What is claimed is:

1. A method of treating a cancer tumor or cancer cells in a subject in need of such therapy, the method comprising the steps of:
    administering to the subject a composition comprising at least one protein-carbon nanotube complex, the at least one protein-carbon nanotube complex comprising a protein or peptide covalently linked to a single-walled carbon nanotube (SWNT), wherein the SWNT is semiconducting and nonmetallic and wherein the protein or peptide of the at least one protein-carbon nanotube complex comprises a binding site that specifically binds to an external receptor or binding site on a tumor vasculature endothelial cell or on a cancer cell in the said subject, and wherein the SWNT of the composition comprises at least 25% of a single type of (n,m) structure; and
    exposing the subject to electromagnetic radiation, thereby causing an elevation of the temperature of the SWNT of the at least one protein-carbon nanotube complex to a temperature which induces damage to and/or death of the tumor vasculature endothelial cell or cancer cell to which the at least one protein-carbon nanotube complex is bound.

2. The method of claim 1, wherein the external receptor or binding site is specific for the tumor vasculature endothelial cells or cancer cells.

3. The method of claim 1, wherein the at least one protein-carbon nanotube complex comprises at least one SWNT having a (n,m) structure selected from the group consisting of (6,5), (7,6), (8,7), (7,5), (8,6), (9,7), and (9,8).

4. The method of claim 1, wherein the composition comprises a plurality of the protein-carbon nanotube complexes.

5. The method of claim 1, wherein the composition comprises at least 25% of a single type of protein-carbon nanotube complex.

6. The method of claim 1, wherein the SWNT of the composition comprises at least 50% of a single type of (n,m) structure.

7. The method of claim 1, wherein the external receptor or binding site is at least one of phosphatidylserine, phosphatidylinositol, phosphatidic acid, and phosphatidylglycerol.

8. The method of claim 1, wherein the covalent linkage of the binding protein or peptide to the SWNT is via a linker comprising a cellulose derivative .

9. The method of claim 8, wherein the cellulose derivative is carboxymethylcellulose, hydroxymethylcellulose, or hydroxypropylcellulose.

10. The method of claim 1, wherein the absorbable wavelength of electromagnetic radiation is near-infrared wavelength.

11. The method of claim 1, wherein the absorbable wavelength is 980 nm±50 nm or 1120 nm±50 nm.

12. The method of claim 1, wherein the SWNT of the protein-carbon nanotube complex has an S11 transition of at least 50% of background.

13. The method of claim 1, wherein the protein of the protein-carbon nanotube complex is an annexin.

14. The method of claim 1, further comprising the step of administering an immunostimulant to the patient.

15. A carbon nanotube composition, comprising:
at least one protein-carbon nanotube complex comprising a protein or peptide covalently linked to a single-walled carbon nanotube (SWNT), wherein the SWNT is semiconducting and nonmetallic, wherein the protein or peptide of the at least one protein-carbon nanotube complex comprises a binding site that specifically binds to an external receptor or binding site on a tumor vasculature endothelial cell and/or on a cancer cell, and wherein when a subject to which the composition has been administered is exposed to a light wavelength absorbable by the SWNT, the temperature of the SWNT of the at least one protein-carbon nanotube complex is elevated to a temperature which induces damage to and/or death of the cell to which the at least one protein-carbon nanotube complex is bound, and wherein the SWNT of the composition comprises at least 25% of a single type of (n,m) structure.

16. The composition of claim 15, wherein the at least one protein-carbon nanotube complex comprises at least one SWNT having a (n,m) structure selected from the group consisting of (6,5), (7,6), (8,7), (7,5), (8,6), (9,7), and (9,8).

17. The composition of claim 15, wherein the composition comprises a plurality of the protein-carbon nanotube complexes.

18. The composition of claim 15, wherein the composition comprises at least 25% of a single type of protein-carbon nanotube complex.

19. The composition of claim 15, wherein the SWNT of the composition comprises at least 40% of a single type of (n,m) structure.

20. The composition of claim 15, wherein the absorbable wavelength is 980 nm±50 nm or 1120 nm±50 nm.

21. The composition of claim 15, wherein the protein of the protein-carbon nanotube complex is an annexin.

22. The composition of claim 15, wherein the SWNT of the composition comprises at least 50% of a single type of (n,m) structure.

23. The composition of claim 15, wherein the SWNT of the composition comprises at least 75% of a single type of (n,m) structure.

24. The composition of claim 15, wherein the covalent linkage of the binding protein or peptide to the SWNT is via a linker.

25. The composition of claim 15, wherein the at least 25% of a single type of (n,m) structure is a (6,5) structure.

* * * * *

UNITED STATES PATENT AND TRADEMARK OFFICE
CERTIFICATE OF CORRECTION

PATENT NO. : 9,504,745 B2
APPLICATION NO. : 14/100892
DATED : November 29, 2016
INVENTOR(S) : Roger G. Harrison, Jr., Damiel E. Resasco and Luis Filipe Ferreira Neves It is certified that error appears in the above-identified patent and that said Letters Patent is hereby corrected as shown below:

In the Specification
Column 16, Line 62: Delete "unabsorbed" and replace with -- unadsorbed --

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial sequence
<220> FEATURE:
<223> OTHER INFORMATION: motif sequence

<400> SEQUENCE: 1

His Trp Gly Phe
1

<210> SEQ ID NO 2
<211> LENGTH: 10
<212> TYPE: PRT
<213> ORGANISM: Artificial sequence
<220> FEATURE:
<223> OTHER INFORMATION: Completely synthesized.

<400> SEQUENCE: 2

Cys Thr Thr His Trp Gly Phe Thr Leu Cys
1               5                   10
```